US 8,177,729 B2

(12) United States Patent
Hibner et al.

(10) Patent No.: US 8,177,729 B2
(45) Date of Patent: *May 15, 2012

(54) METHOD OF TETHERLESS BIOPSY DEVICE OPERATION

(75) Inventors: John A. Hibner, Mason, OH (US); Patrick A. Mescher, Bellbrook, OH (US); Edward A. Rhad, Fairfield, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 189 days.

This patent is subject to a terminal disclaimer.

(21) Appl. No.: 12/542,217

(22) Filed: Aug. 17, 2009

(65) Prior Publication Data

US 2010/0317995 A1 Dec. 16, 2010

Related U.S. Application Data

(63) Continuation of application No. 12/483,305, filed on Jun. 12, 2009.

(51) Int. Cl.
*A61B 10/00* (2006.01)
*A61B 17/32* (2006.01)

(52) U.S. Cl. ...................... 600/567; 606/170

(58) Field of Classification Search .......... 600/562–568; 606/167, 170, 176, 179, 180, 184–185; 91/4 R
See application file for complete search history.

(56) References Cited

U.S. PATENT DOCUMENTS

| | | | |
|---|---|---|---|
| 5,526,822 A | 6/1996 | Burbank et al. | |
| 6,007,497 A | 12/1999 | Huitema | |
| 6,086,544 A | 7/2000 | Hibner et al. | |
| 6,626,849 B2 | 9/2003 | Huitema et al. | |
| 7,252,641 B2 * | 8/2007 | Thompson et al. | 600/568 |
| 7,442,171 B2 | 10/2008 | Stephens et al. | |
| 7,497,833 B2 | 3/2009 | Miller | |
| 2006/0074345 A1 | 4/2006 | Hibner | |
| 2007/0032742 A1 | 2/2007 | Monson et al. | |
| 2007/0149894 A1 | 6/2007 | Heske et al. | |

(Continued)

FOREIGN PATENT DOCUMENTS

| | | |
|---|---|---|
| EP | 1 642 533 | 4/2006 |
| EP | 1 932 482 | 6/2008 |

OTHER PUBLICATIONS

U.S. Appl. No. 12/335,578, filed Dec. 16, 2008, Parihar et al.

(Continued)

*Primary Examiner* — Brian Szmal
*Assistant Examiner* — Vivekram P Bellur
(74) *Attorney, Agent, or Firm* — Frost Brown Todd LLC

(57) ABSTRACT

A method of biopsy device operation comprises rotating a first rotating member at a first rotational speed to rotate a cutter. A second rotating member is rotated at a second rotational speed to translate the cutter. The first and second members are rotated simultaneously and in the same direction. The first rotating member rotates with the cutter, while the second rotating member rotates about the first rotating member. The difference between the first and second rotational speeds, as well as threaded engagement between the first and second rotating members, provides the translation of the cutter. A method of biopsy device operation also comprises moving a shuttle valve slider to selectively vent or seal the second lumen of a needle. The shuttle valve slider is responsive to translation of the cutter, though some degree of lost motion is provided between the shuttle valve slider and the cutter.

20 Claims, 16 Drawing Sheets

U.S. PATENT DOCUMENTS

2007/0239067 A1    10/2007    Hibner et al.
2008/0195066 A1    8/2008    Speeg et al.
2008/0214955 A1    9/2008    Speeg et al.
2009/0171242 A1    7/2009    Hibner

OTHER PUBLICATIONS

U.S. Appl. No. 12/337,874, filed Dec. 18, 2008, Parihar et al.
U.S. Appl. No. 12/337,911, filed Dec. 18, 2008, Prihar et al.
U.S. Appl. No. 12/337,942, filed Dec. 18, 2008, Parihar et al.
U.S. Appl. No. 12/337,997, filed Dec. 18, 2008, Parihar.
U.S. Appl. No. 12/483,305, filed Jun. 12, 2009, Hibner et al.
U.S. Appl. No. 12/541,437, filed Aug. 14, 2009, Hibner et al.
European Search Report dated Sep. 29, 2010 for Application No. EP 10251076.

* cited by examiner

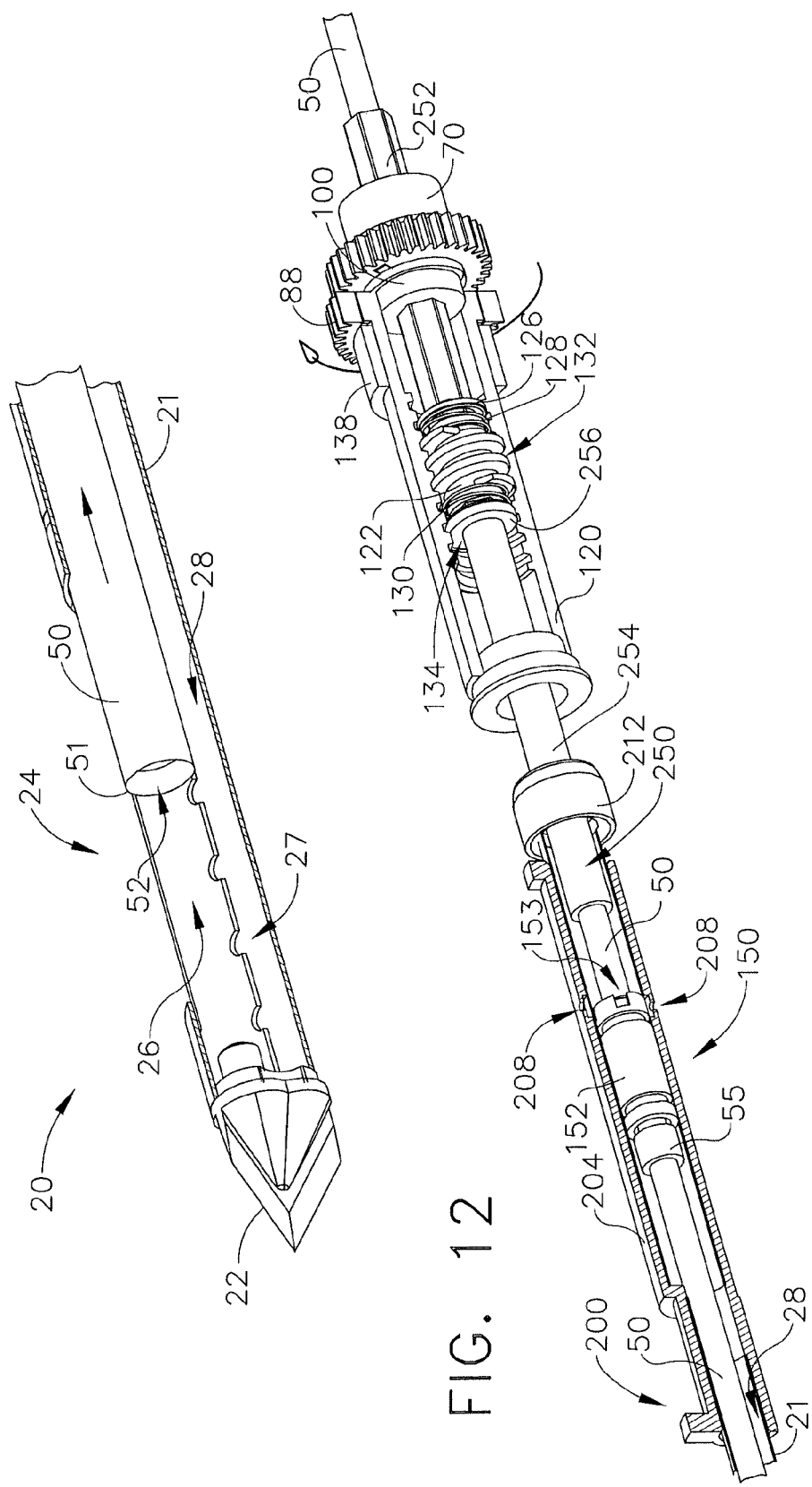

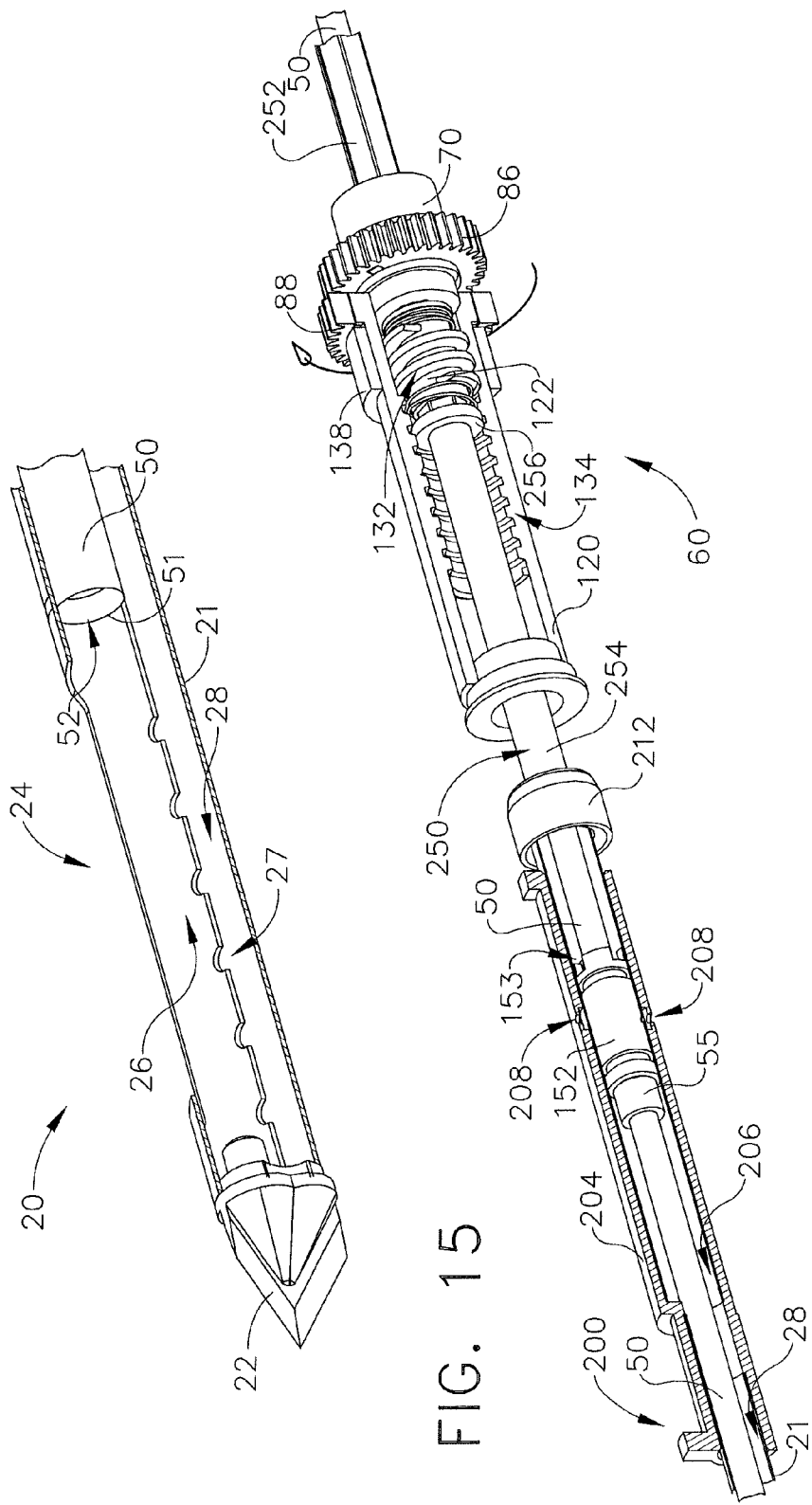

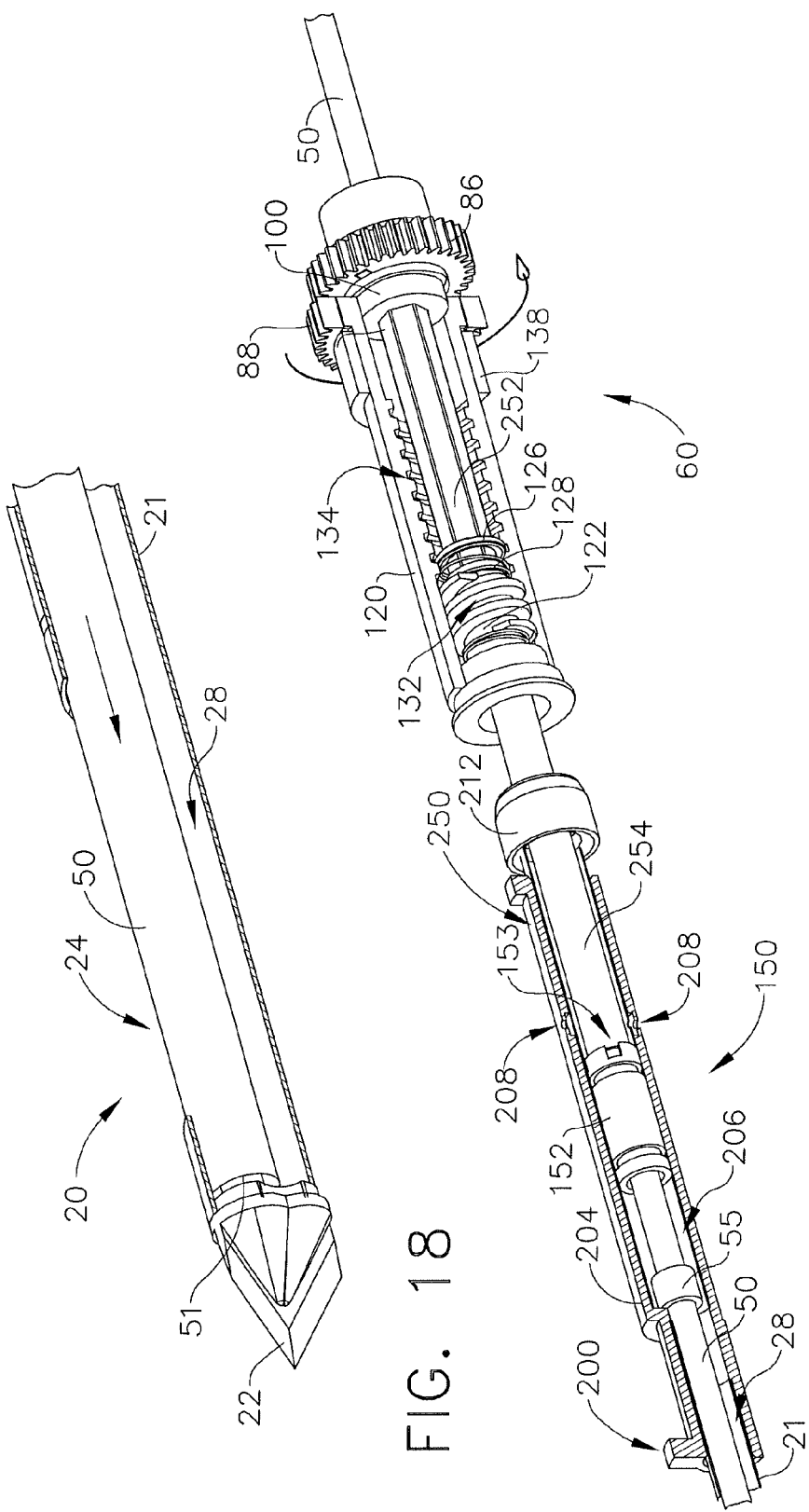

METHOD OF TETHERLESS BIOPSY DEVICE OPERATION

PRIORITY

This application is a continuation of U.S. Non-Provisional patent application Ser. No. 12/483,305, entitled, "Tetherless Biopsy Device with Reusable Portion," filed Jun. 12, 2009, the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pat. Pub. No. 2009/0171242 , entitled "Clutch and Valving System for Tetherless Biopsy Device, "published Jul 2, 2009; U.S. Pat. Pub. No. 2010/0152610 , entitled "Hand Actuated Tetherless Biopsy Device with Pistol Grip," published Jun. 17, 2010; and U.S. Pat. Pub. No. 2010/0160819 , entitled "Biopsy Device with Central Thumbwheel, "published Jun. 24, 2010. The disclosure of each of the above-cited U.S. Patents, U.S. Patent Application Publications, and U.S. Non-Provisional Patent Application is incorporated by reference herein.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 12 depicts a perspective cross-sectional view of a needle portion of the biopsy device of FIG. 1, with the cutter in a partially retracted position;

FIG. 13 depicts a perspective cross-sectional view of the components of FIG. 10, with the cutter in the partially retracted position of FIG. 12;

FIG. 15 depicts a perspective cross-sectional view of a needle portion of the biopsy device of FIG. 1, with the cutter in a retracted position;

FIG. 16 depicts a perspective cross-sectional view of the components of FIG. 10, with the cutter in the retracted position of FIG. 15;

FIG. 18 depicts a perspective cross-sectional view of a needle portion of the biopsy device of FIG. 1, with the cutter re-advanced to the distal-most position of FIG. 9;

FIG. 19 depicts a perspective cross-sectional view of the components of FIG. 10, with the cutter re-advanced to the distal-most position of FIG. 9.

Figure 1:
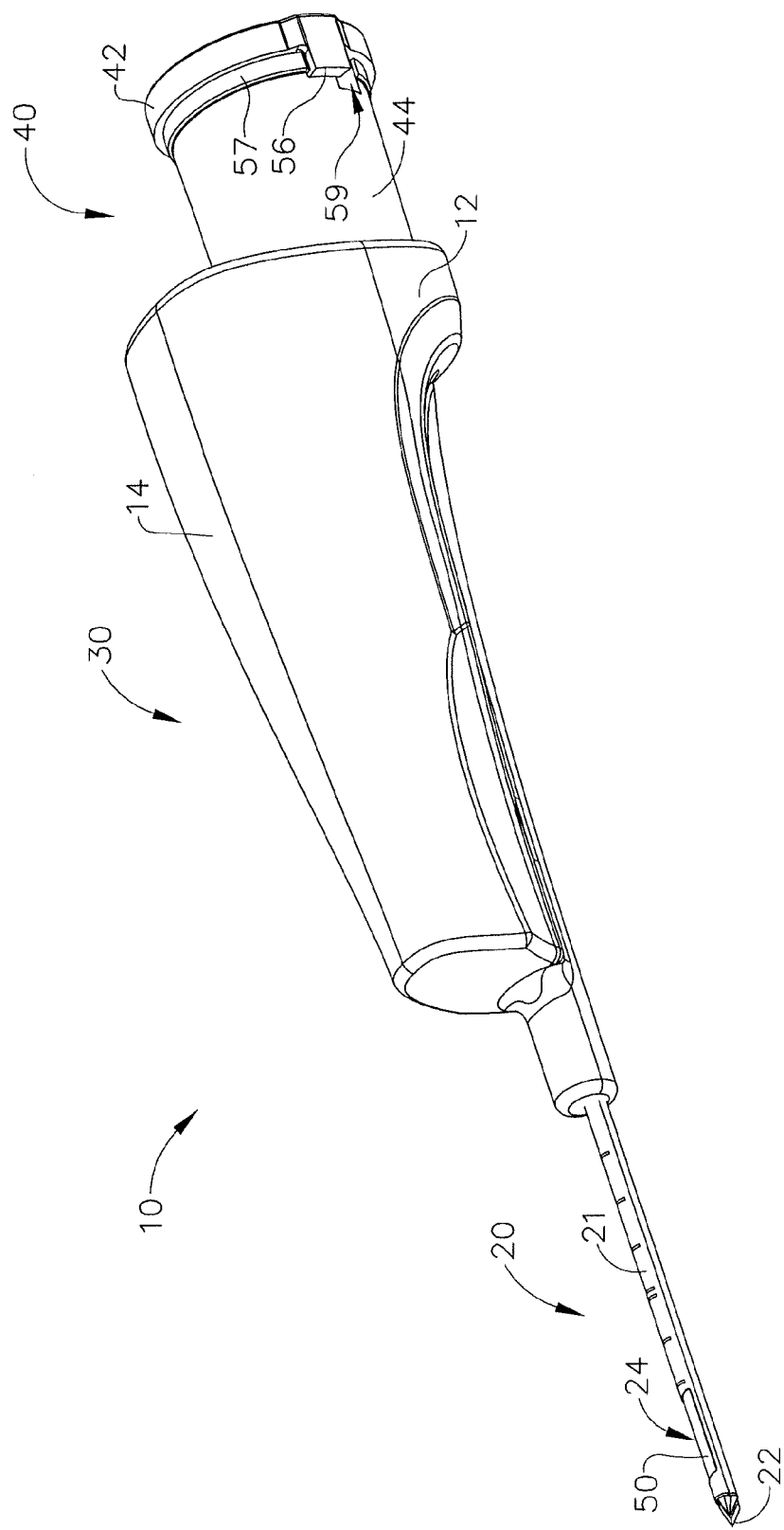
FIG. 1 depicts a perspective view of an exemplary biopsy device.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Overview

Figure 2:
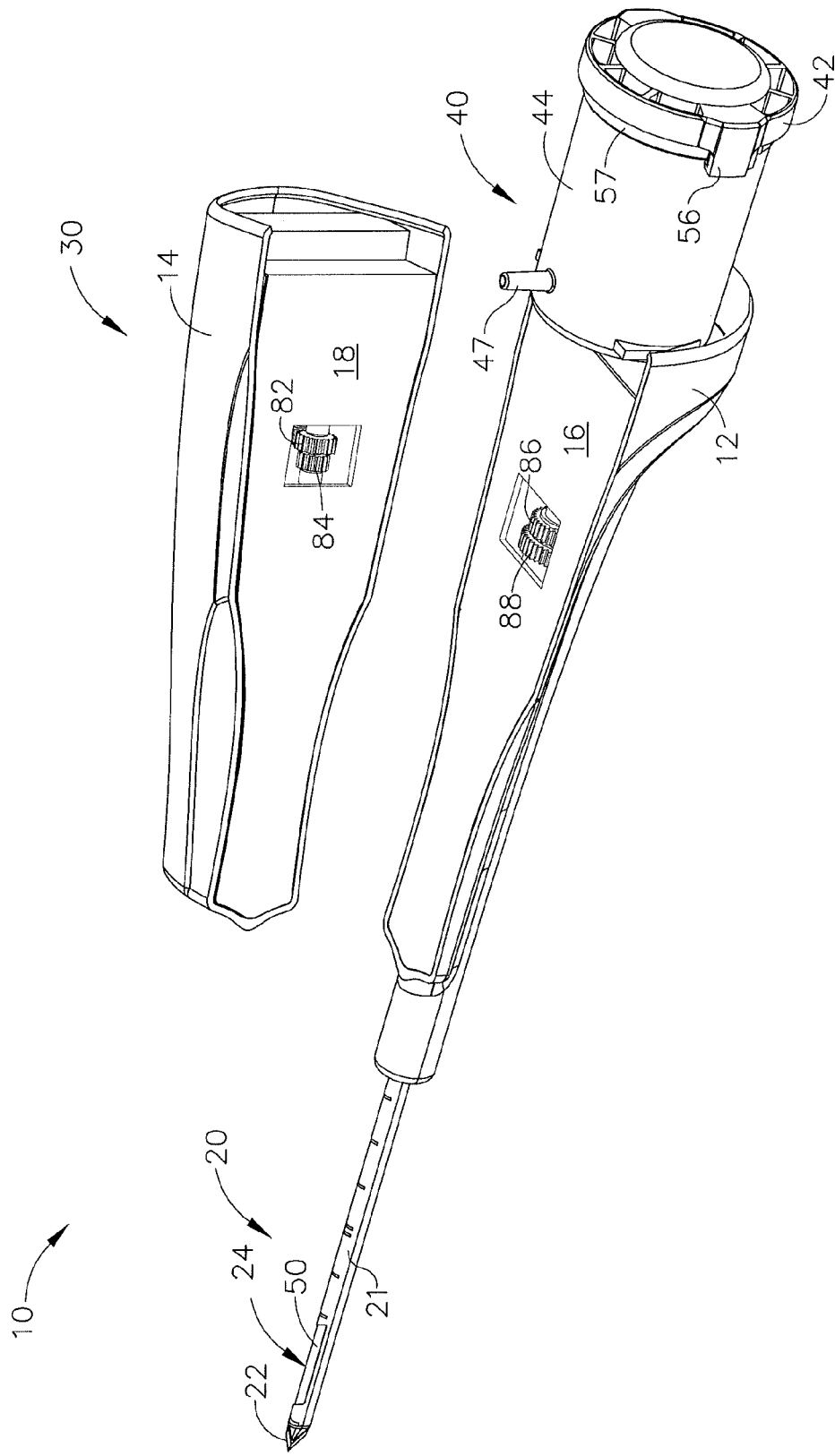
FIG. 2 depicts a perspective view of the biopsy device of FIG. 1, with a probe portion separated from a holster portion.
Figure 3:
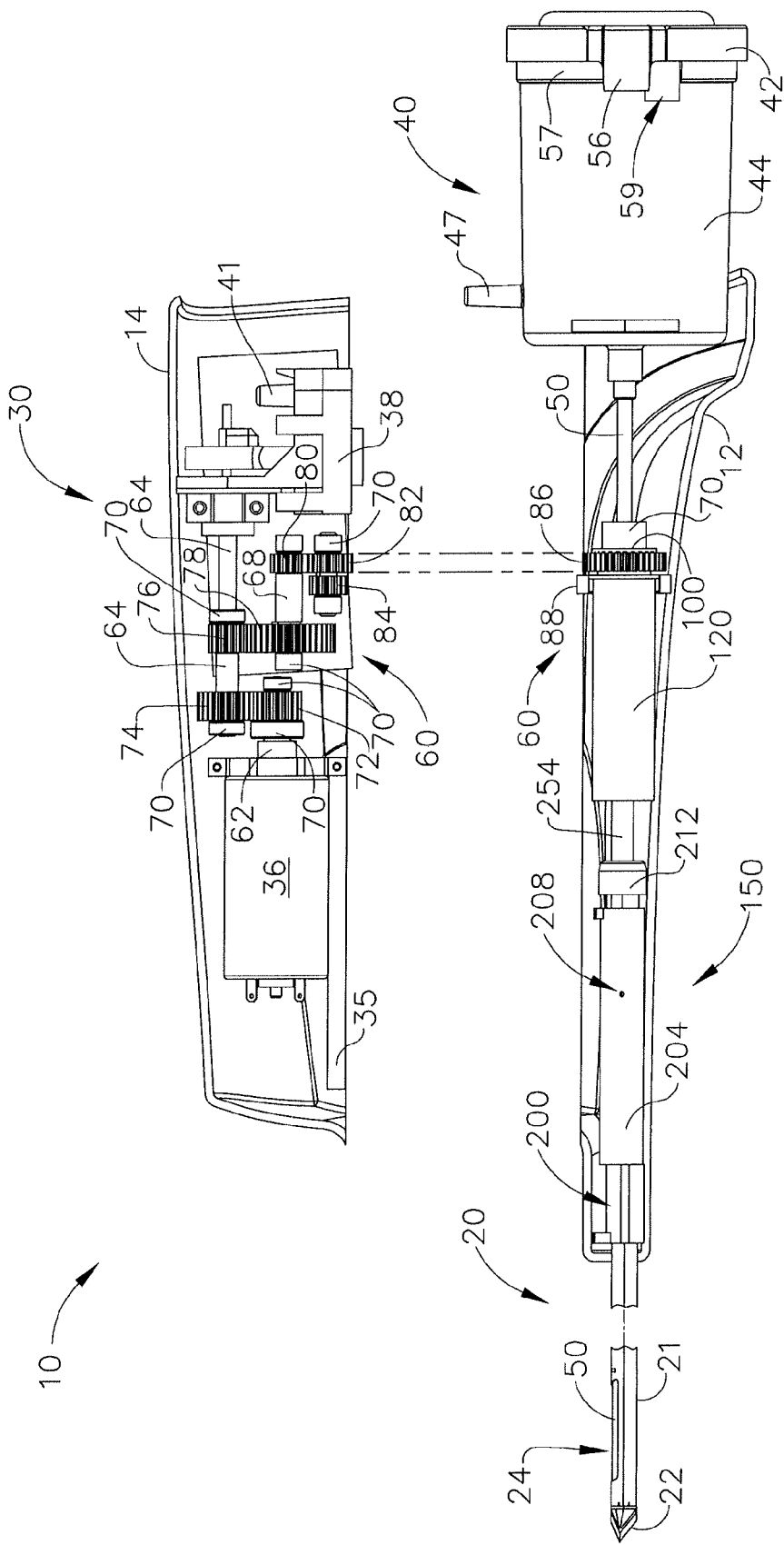
FIG. 3 depicts a side cross-sectional view of the biopsy device of FIG. 1, with the probe portion separated from the holster portion.

As shown in FIGS. 1-3 (among others), an exemplary biopsy device (10) comprises a needle (20), a body (30), and a tissue sample holder (40). In particular, needle (20) extends distally from the distal portion of body (30), while tissue sample holder (40) extends proximally from the proximal portion of body (30). Body (30) is sized and configured such that biopsy device (10) may be operated by a single hand of a user. In particular, and as described in greater detail below, a user may grasp body (30) with a single hand, insert needle (20) into a patient's breast, and collect one or a plurality of tissue samples from within the patient's breast, all with just using a single hand. Alternatively, a user may grasp body (30) with more than one hand and/or with any desired assistance. In some settings, the user may capture a plurality of tissue samples with just a single insertion of needle (20) in the patient's breast. Such tissue samples may be pneumatically deposited in tissue sample holder (40), as described in greater detail below, then retrieved from tissue sample holder (40) for analysis.

Body (30) of the present example comprises a probe (12) and a holster (14). As shown in FIGS. 2-3, and as described in greater detail below, probe (12) is separable from holster (14). In particular, probe (12) and holster (14) may be removably coupled using bayonet mounts (not shown) or any other suitable structures or features. Use of the term "holster" herein should not be read as requiring any portion of probe (12) to be inserted into any portion of holster (14). Indeed, in some variations of biopsy device (10), probe (12) may simply sit on holster (14). In some other variations, a portion of holster (14) may be inserted into probe (12). Furthermore, in some biopsy devices (10), probe (12) and holster (14) may be of unitary or integral construction, such that the two components cannot be separated. By way of example only, in versions where probe (12) and holster (14) are provided as separable components, probe (12) may be provided as a disposable component, while holster (14) may be provided as a reusable component. Still other suitable structural and functional relationships between probe (12) and holster (14) will be apparent to those of ordinary skill in the art in view of the teachings herein.

Some variations of biopsy device (10) may include one or more sensors (not shown), in probe (12) and/or in holster (14), that is/are configured to detect when probe (12) is coupled with holster (14). Such sensors or other features may further be configured to permit only certain types of probes (12) and holsters (14) to be coupled together. In addition or in the alternative, such sensors may be configured to disable one or more functions of probes (12) and/or holsters (14) until a suitable probe (12) and holster (14) are coupled together. Of course, such sensors and features may be varied or omitted as desired.

While examples described herein refer to the acquisition of biopsy samples from a patient's breast, it should be understood that biopsy device (10) may be used in a variety of other procedures for a variety of other purposes and in a variety of other parts of a patient's anatomy.

Exemplary Needle

Figure 8:
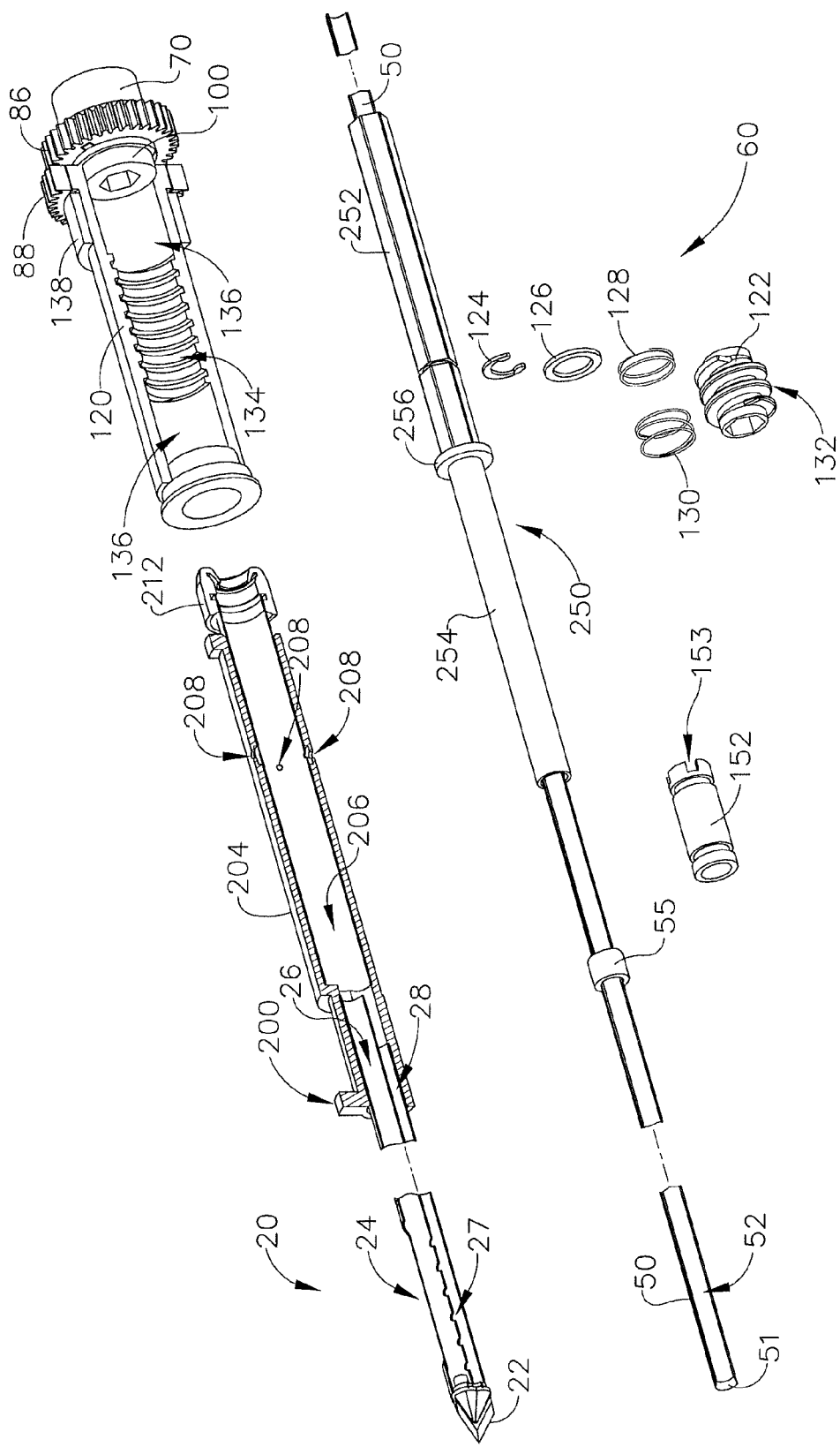
FIG. 8 depicts an exploded view of cutter and needle components of the biopsy device of FIG. I, with portions shown in cross-section.
Figures 9, 10:
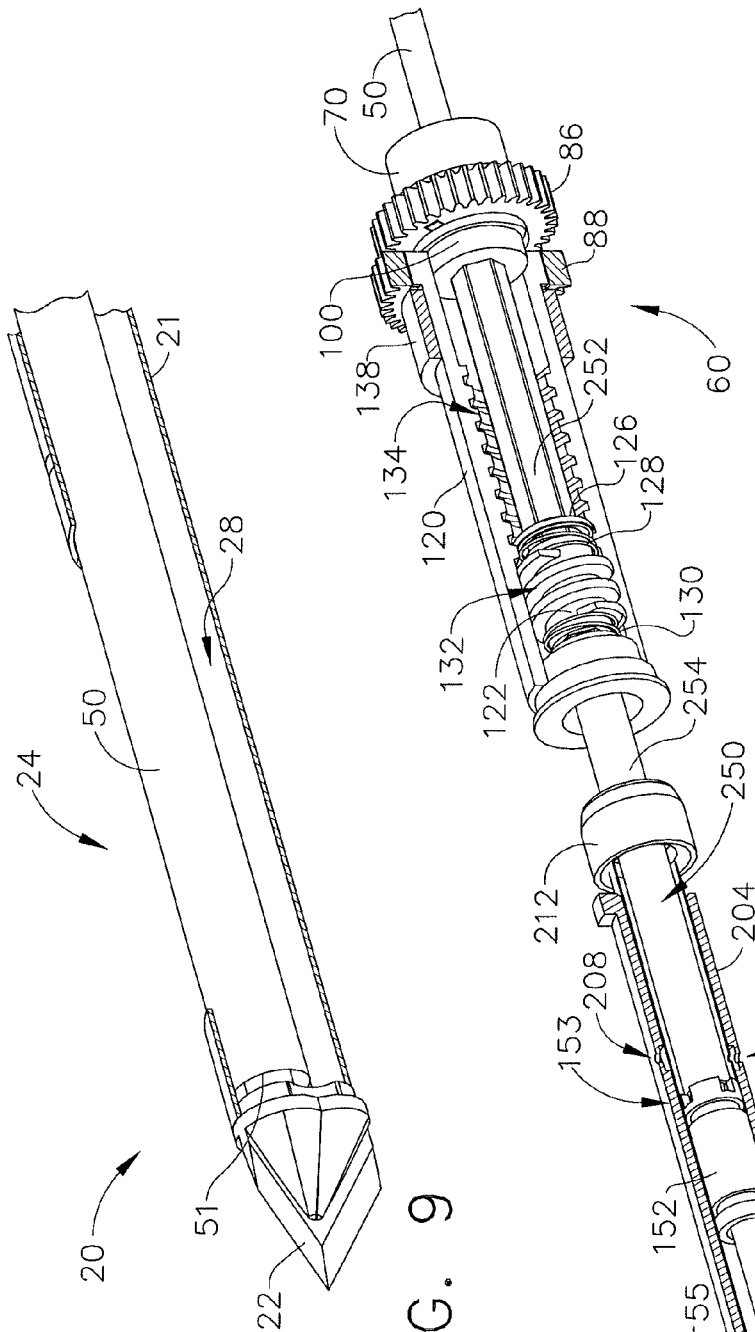
FIG. 9 depicts a perspective cross-sectional view of a needle portion of the biopsy device of FIG. 1, with the cutter in a distal-most position.
FIG. 10 depicts a perspective cross-sectional view of cutter actuation mechanism and valve mechanism components of the biopsy device of FIG. 1, with the cutter in the distal-most position of FIG. 9.

As shown in FIGS. 8-9 (among others), needle (20) of the present example comprises a cannula (21) with a tissue piercing tip (22), a lateral aperture (24), a first lumen (26), and a second lumen (28). Tissue piercing tip (22) is configured to pierce and penetrate tissue, without requiring a high amount of force, and without requiring an opening to be pre-formed in the tissue prior to insertion of tip (22). A cutter (50) is disposed in first lumen (26), and is operable to rotate and translate within first lumen (26) as will be described in greater detail below. Lateral aperture (24) is located proximal to tip (22), is in fluid communication with first lumen (26), and is configured to receive tissue when needle (20) is inserted in a breast and when a cutter (50) is retracted as will also be described in greater detail below. A plurality of openings (27) provide fluid communication between first and second lumens (26, 28). A plurality of external openings (not shown) may also be formed in needle (20), and may be in fluid communication with second lumen (28). Examples such external openings are disclosed in U.S. Pub. No. 2007/0032742, entitled "Biopsy Device with Vacuum Assisted Bleeding Control," published Feb. 8, 2007, the disclosure of which is incorporated by reference herein. Of course, as with other components described herein, such external openings are merely optional.

Figure 11:
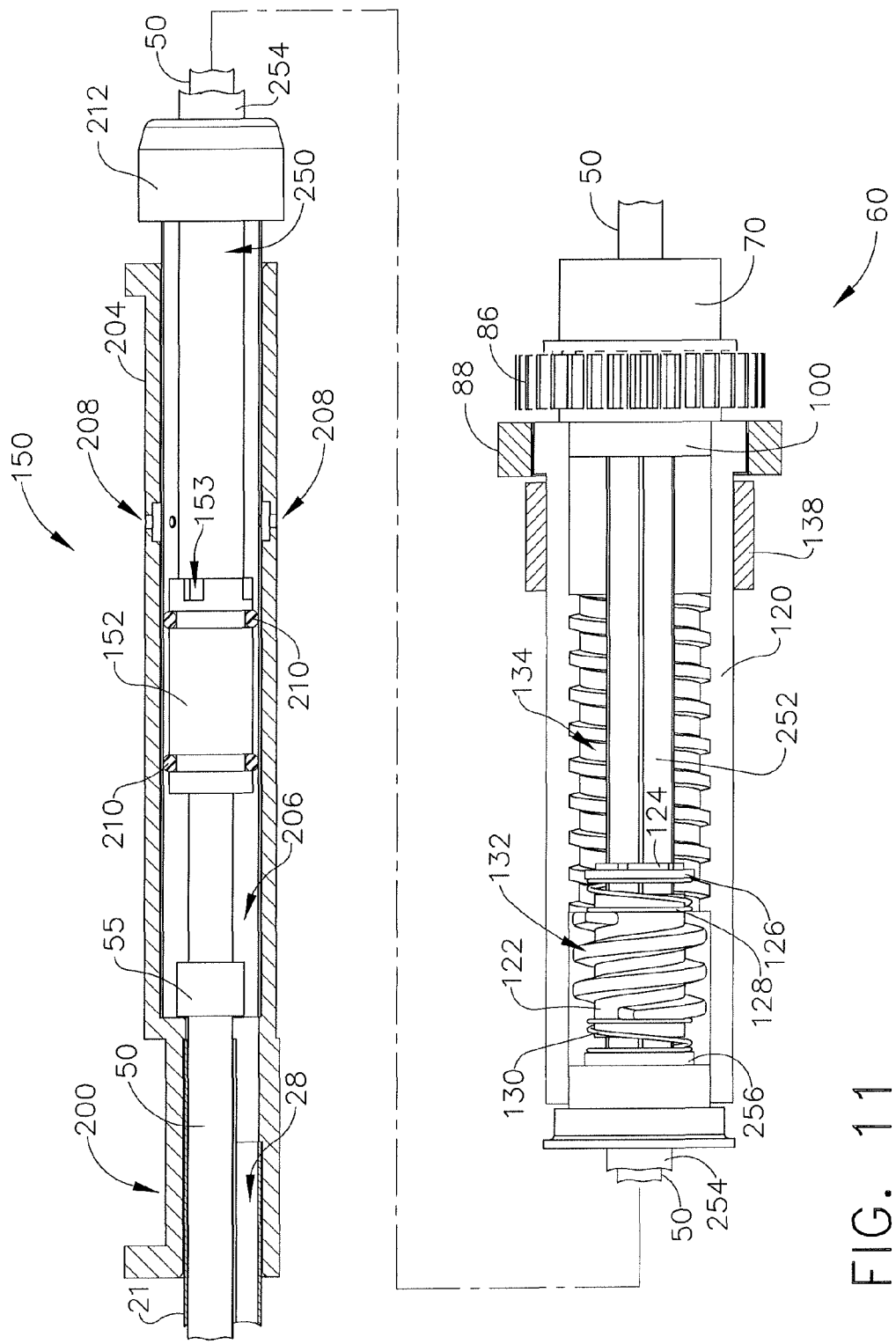
FIG. 11 depicts a side cross-sectional view of the components of FIG. 10, with the cutter in the distal-most position of FIG. 9.

Needle (20) of the present example further comprises a hub (200), as shown in FIGS. 8 and 10-11 (among others). Hub (200) may be formed of plastic that is overmolded about needle (20) or otherwise secured to needle (20), such that hub (200) is unitarily secured to needle (20). Alternatively, hub (200) may be formed of any other suitable material through any suitable process and may have any other suitable relationship with needle (20).

Hub (200) of the present example comprises a sleeve portion (204). Sleeve portion (204) extends integrally into probe portion (12) of body (30). As shown in FIGS. 8 and 10-11 (among others), sleeve portion (204) defines a hollow interior (206), which is in fluid communication with second lumen (28) of needle (20). Sleeve portion (204) also defines a plurality of openings (208), which are radially spaced about the perimeter of sleeve portion (204) at a common longitudinal position, and which are in fluid communication with hollow interior (206). Openings (208) are exposed to ambient air, such that openings (208) provide a vent in the present example. Openings (208) are selectively fluidly coupled with second lumen (28) of needle (20) in this example, as will be described in greater detail below. In particular, openings (208) are selectively coupled with second lumen (28) during use of biopsy device (10), to selectively provide venting to second lumen (28). A pair of o-rings (210) are positioned about a shuttle valve slider (152), to substantially seal second lumen (28) relative to openings (208) when second lumen (28) is not to be vented, depending on the longitudinal position of slider (152) as will be described in greater detail below. A seal (212) is also provided at the proximal end of sleeve (204), at the interface of cutter (50) and sleeve (204). Seal (212) is configured to substantially seal the interface of cutter (50) and sleeve (204), even as cutter (50) rotates and translates relative to sleeve (204). In particular, seal (212) sealingly engages a smooth portion (254) of a sleeve (250) that is unitarily secured to cutter (50) as will be described in greater detail below.

It should be understood that, as with other components described herein, needle (20) may be varied, modified, substituted, or supplemented in a variety of ways; and that needle (20) may have a variety of alternative features, components, configurations, and functionalities. By way of example only, needle (20) may simply lack second lumen (28) altogether in some versions, such that first lumen (26) is the only lumen defined by needle (20). As another merely exemplary alternative, biopsy device (10) may be configured such that needle (20) may be fired distally relative to body (30), such as to assist in penetration of tissue. Such firing may be provided by one or more actuators (e.g., solenoid, pneumatic cylinder/piston, etc.), by one or more springs, or in any other suitable fashion. Other suitable alternative versions, features, components, configurations, and functionalities of needle (20) will be apparent to those of ordinary skill in the art in view of the teachings herein.

Similarly, other suitable modifications to other components of biopsy device (10) that may be made in accordance with variations of needle (20) (e.g., modifying or omitting valve mechanism (150) in versions where second lumen (28) is omitted from needle (20), etc.) will be apparent to those of ordinary skill in the art in view of the teachings herein.

Exemplary Body

Figure 4:
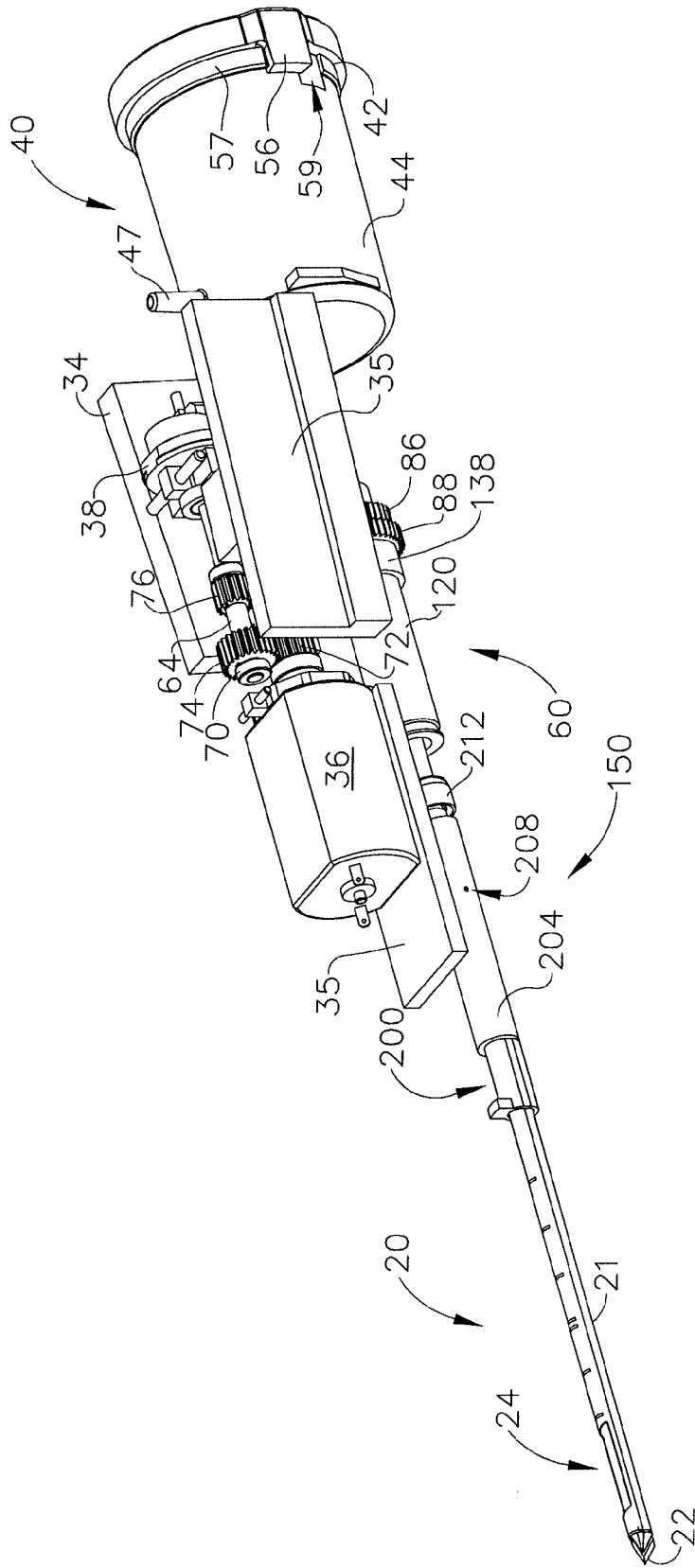
FIG. 4 depicts a perspective view of the biopsy device of FIG. 1, with housing components removed.
Figure 6:
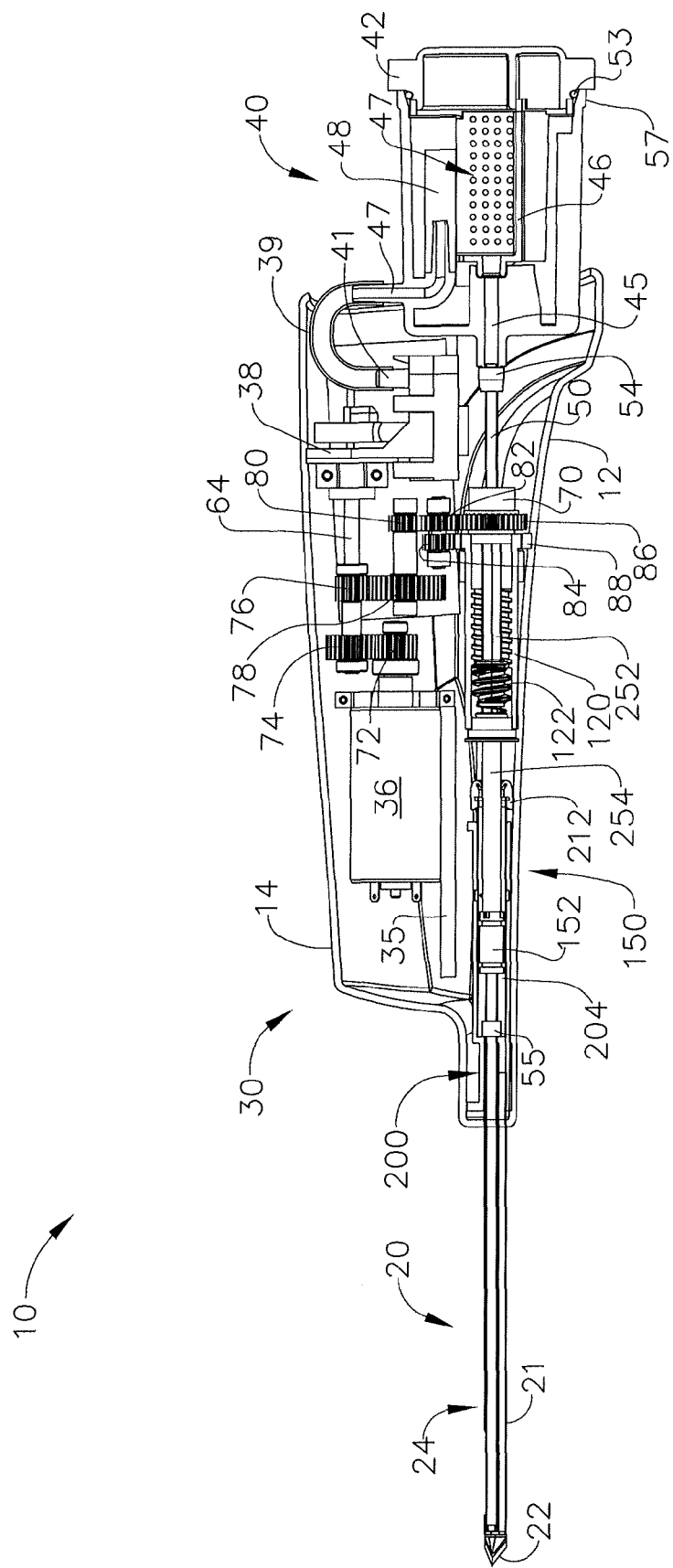
FIG. 6 depicts a side cross-sectional view of the biopsy device of FIG. 1.
Figure 7:
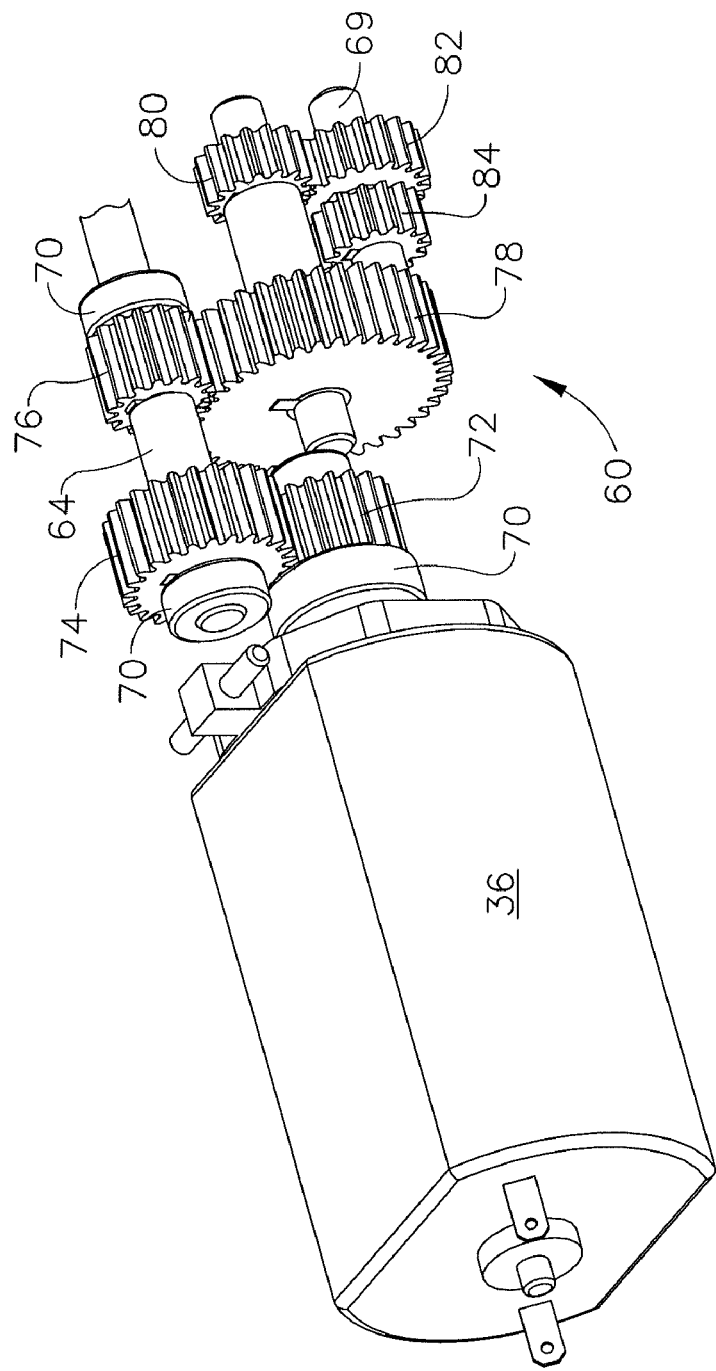
FIG. 7 depicts a perspective view of drive train components of the biopsy device of FIG. 1.

As noted above, body (30) of the present example comprises a probe portion (12) and a holster portion (14). As shown in FIGS. 3-4 and 6 (among others), a battery (34), a pair of circuit boards (35), a motor (36), and a vacuum pump (38) are provided within probe portion (12). Battery (34) may comprise a rechargeable battery, a non-rechargeable battery, or any other type of battery.

For instance, if battery (34) is rechargeable, biopsy device (10) may permit recharging of battery (34) by inserting holster (14) into a recharging station, by allowing removal of battery (34) for recharging, by providing a port for coupling a power cord with holster (14) to allow operation of biopsy device (10) while simultaneously recharging battery (34), or in any other suitable fashion. In addition, battery (34) may provide any suitable voltage, and may be configured to provide power for at least five biopsy procedures or any other suitable number of procedures before requiring a recharge or replacement. In other versions, biopsy device (10) is powered by some other source, such as a conventional AC power source or piece of capital equipment, such that battery (34) is merely optional. Battery (34) is coupled with motor (36) via circuit boards (35) and a trigger button (not shown) in the present example.

As shown in FIGS. 3-6, motor (36) of the present example is in mechanical communication with vacuum pump (38) and a cutter actuation mechanism (60). In particular, motor (36) is operable to simultaneously activate vacuum pump (38) and cutter actuation mechanism (60) when motor (36) is activated. Alternatively, vacuum pump (38) and cutter rotation mechanism (60) may be activated in any other suitable fashion. By way of example only, vacuum pump (38) and/or cutter rotation mechanism (60) may be activated manually and/or by separate motors and/or in any other suitable fashion. Motor (36) of the present example comprises a conventional DC motor. However, it should be understood that motor (36) may alternatively comprise a pneumatic motor (e.g., with impeller, etc.), a pneumatic linear actuator, an electromechanical linear actuator, or a variety of other types of movement-inducing devices. Various suitable ways in which other types of movement-inducing devices may be incorporated into biopsy device (10) will be apparent to those of ordinary skill in the art in view of the teachings herein.

As shown in FIGS. 3-7, a drive shaft (62) extends from motor (36), and is rotationally driven by motor (36). A pair of bearings (70) and a drive gear (72) are positioned about drive shaft (62). Bearings (70) support drive shaft (62), while drive gear (72) rotates unitarily with drive shaft (62). In particular, motor (36) may be selectively activated to rotate drive shaft (62) and drive gear (72) in either rotational direction. Drive gear (72) meshes with a second gear (74), which is unitarily secured to a second shaft (64). Second shaft (64) also includes associated bearings (70) and a third gear (76). Second shaft (64) and gears (74, 76) rotate unitarily, such that motor (36) is operable to rotatingly drive second shaft (64) and gears (74, 76) via drive shaft (62) and drive gear (72).

Vacuum pump (38) of the present example comprises a conventional diaphragm pump. In particular, a second shaft (64), which is rotationally driven by motor (36) as described above, is coupled with an eccentric disk (not shown—e.g., a device for converting circular motion into rectilinear motion, comprising a disk fixed off-center to second shaft (64)), which is configured to cause a rod (not shown—e.g., the rod may be coupled with or otherwise driven by the eccentric disk) of vacuum pump (38) to reciprocate as motor (36) and shafts (62, 64) rotate. This rod of vacuum pump (38) drives a diaphragm (not shown) of vacuum pump (38) as the rod reciprocates, causing vacuum pump (38) to induce a vacuum. It should be understood that vacuum pump (38) of the present example operates in the same way regardless of which direction motor (36) rotates. Of course, any other suitable type of vacuum pump may be used. Vacuum pump (38) of the present example is operable to induce a vacuum in tissue sample holder (40) when vacuum pump (38) is activated, as will be described in greater detail below. Cutter actuation mechanism (60) is operable to rotate and translate cutter (50) when cutter rotation mechanism (60) is activated, as will also be described in greater detail below. In particular, cutter actuation mechanism (60) is operable to cause cutter (50) to rotate within first lumen (26) and concomitantly cause cutter (50) to translate within first lumen (26), such as to sever a biopsy sample from tissue protruding through lateral aperture (24).

It should be understood that, as with other components described herein, body (30) may be varied, modified, substituted, or supplemented in a variety of ways; and that body (30) may have a variety of alternative features, components, configurations, and functionalities. Suitable alternative versions, features, components, configurations, and functionalities of body (30) will be apparent to those of ordinary skill in the art in view of the teachings herein.

Exemplary Valve Mechanism

As shown in FIGS. 5-6, 8, and 10-11 (among others), biopsy device (10) also includes a valve mechanism (150) in the present example. Valve mechanism (150) of this example comprises shuttle valve slider (152), o-rings (210), and sleeve (204) of needle hub (200). Shuttle valve slider (152) is positioned coaxially about cutter (50), and is configured to translate relative to sleeve (204) and relative to cutter (50). In particular, shuttle valve slider (152) is positioned about cutter (50) longitudinally between the distal end of sleeve (250) and the proximal end of a stop member (55), which is unitarily secured to cutter (50). O-rings (210) are configured to seal the exterior of shuttle valve slider (152) against the interior sidewall of sleeve (204). Shuttle valve slider (152) defines an inner diameter that is greater than the outer diameter defined by cutter (50), such that a gap is provided between the outer diameter of cutter (50) and the inner diameter of shuttle valve slider (152). Such a gap is sufficient to provide longitudinal fluid communication (e.g., atmospheric air, etc.) between the outer diameter of cutter (50) and the inner diameter of shuttle valve slider (152). In addition, the proximal end of shuttle valve slider (152) has notches (153) formed in it, providing an appearance similar to that of a castellated nut or castle nut. The proximal end of shuttle valve slider (152) is also configured to be engaged by the distal end of smooth portion (254) of sleeve (250), such that sleeve (250) may push shuttle valve slider distally as described below. Notches (153) are configured to provide fluid communication to the interior of shuttle valve slider (152), even as the distal end of smooth portion (254) of sleeve (250) engages the proximal end of shuttle valve slider (152).

As described in greater detail below, cutter (50) is configured to rotate and translate relative to body (30), while sleeve (204) remains substantially stationary relative to body (30). As noted above, sleeve (250) and stop member (55) translate unitarily with cutter (50). In addition, stop member (55) and shuttle valve slider (152) are configured such that stop member (55) may push shuttle valve slider (152) proximally when stop member (55) is engaged with shuttle valve slider (152); while sleeve (250) and shuttle valve slider (152) are configured such that sleeve (250) may push shuttle valve slider (152) distally when sleeve (250) is engaged with shuttle valve slider (152). Shuttle valve slider (152) may thus translate within sleeve (250) in accordance with translation of cutter (50) relative to body (30). However, the distance between the distal end of sleeve (250) and the proximal end of stop member (55) is greater than the length of shuttle valve slider (152), such that there is a degree of "lost motion" between shuttle valve slider (152) and cutter (50) as cutter (50) translates in the present example. In other words, shuttle valve slider (152) remains substantially stationary during certain stages of a cutter (50) actuation stroke (see, e.g., FIGS. 12-14), such that shuttle valve slider (1 52) only translates when cutter (50) approaches the distal-most position (see, e.g., FIGS. 18-20) and the proximal-most position (see, e.g., FIGS. 15-17).

Figure 17:
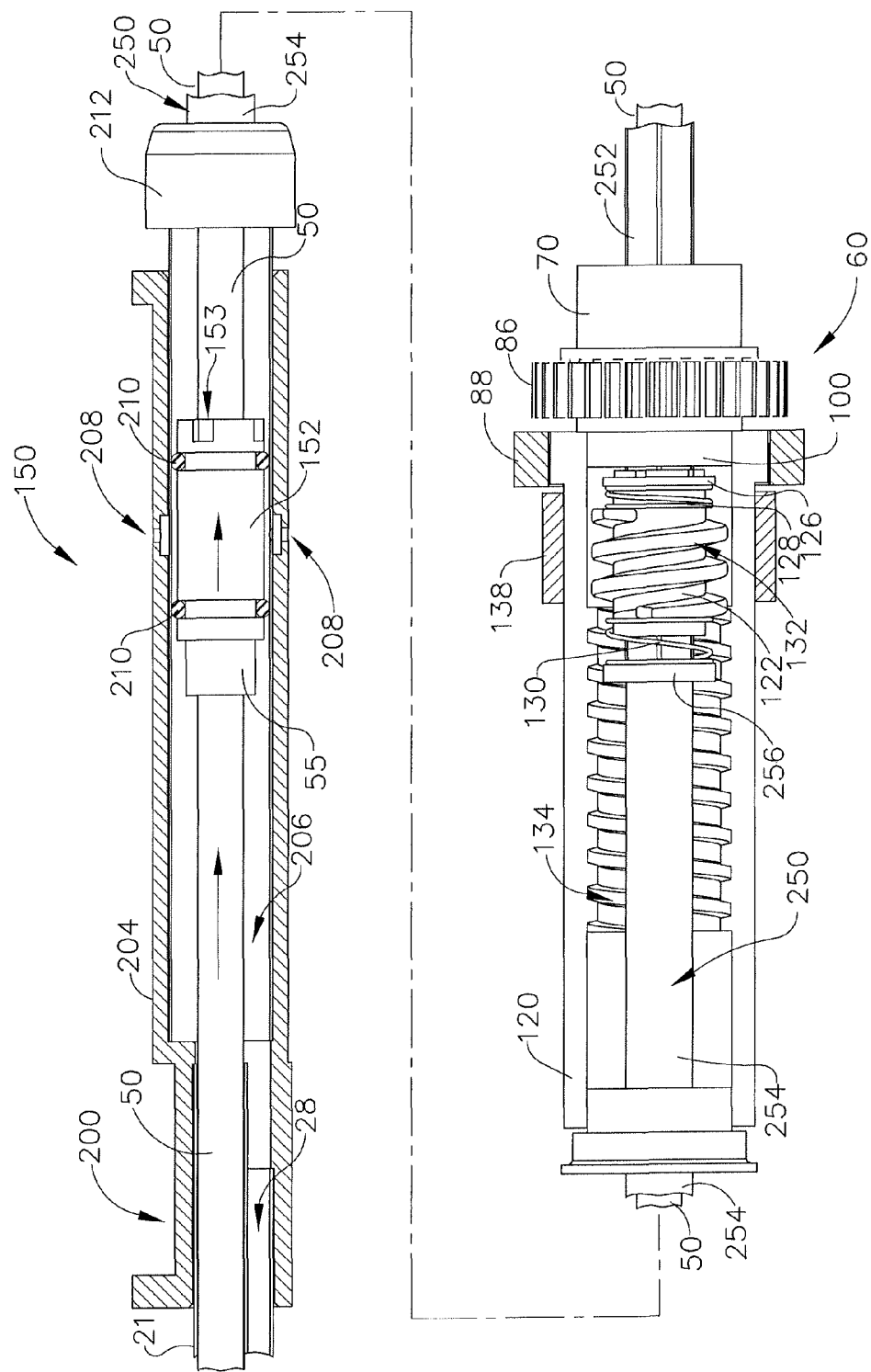
FIG. 17 depicts a side cross-sectional view of the components of FIG. 10, with the cutter in the retracted position of FIG. 15.

As noted above, openings (208) of sleeve (204) communicate with ambient air; and shuttle valve slider (152) is operable to selectively vent second lumen (28) to atmosphere. In particular, shuttle valve slider (152) remains distal to openings (208) when cutter (50) is at a distal-most position (see, e.g., FIGS. 9-11 and 18-20); when cutter (50) is transitioning between the distal-most position and the proximal-most position (see, e.g., FIGS. 12-14); and at latter stages of cutter (50) transitioning from the proximal-most position to the distal-most position. During these stages of operation, second lumen (28) is exposed to ambient air via openings (208) in sleeve (204), notches (153) in shuttle valve slider (152), the gap between the inner diameter of shuttle valve slider (152) and the outer diameter of cutter (50), and the portion of sleeve interior (206) that is distal to shuttle valve slider (152). However, shuttle valve slider (152) and o-rings (210) substantially seal second lumen (28) relative to openings (208) when cutter (50) is in a proximal position, such as is shown in FIGS. 15-17. In particular, when cutter (50) moves to the proximal position, stop member (55) pushes shuttle valve slider (152) proximally such that openings (208) are longitudinally positioned between o-rings (210). O-rings (210) thus substantially seal off openings (208) when openings (208) are between o-rings (210). When cutter (50) begins moving again distally toward the distal-most position, shuttle valve slider (152) remains at this proximal position momentarily, continuing to substantially seal second lumen (28) relative to openings (208), until the distal end of sleeve (250) engages the proximal end of shuttle valve slider (152) and begins pushing shuttle valve slider (152) distally to the point where the proximal-most o-ring (210) is moved distal to openings (208). Once the proximal-most o-ring (210) moves distal to openings (208), second lumen (28) is again vented as noted above. Thus, valve mechanism (150) of the present example substantially seals off second lumen (28) relative to atmosphere when cutter (50) is at a proximal position and when cutter (50) is at initial stages of advancement; while venting second lumen (28) to atmosphere when cutter (50) is at other positions.

It should be understood that, as with other components described herein, valve mechanism (150) may be varied, modified, substituted, or supplemented in a variety of ways; and that valve mechanism (150) may have a variety of alternative features, components, configurations, and functionalities. Suitable alternative versions, features, components, configurations, and functionalities of valve mechanism (150) will be apparent to those of ordinary skill in the art in view of the teachings herein.

Exemplary Tissue Sample Holder

As shown in FIGS. 1-6, tissue sample holder (40) of the present example comprises a cap (42), an outer cup (44), and a filter tray (46). Cup (44) is secured to probe (12) in the present example. Such engagement may be provided in any suitable fashion. Outer cup (44) of the present example is substantially transparent, allowing the user to view tissue samples on filter tray (46), though outer cup (44) may have any other suitable properties if desired.

Outer cup (44) is in fluid communication with cutter lumen (52) and with vacuum pump (38) in the present example. In particular, outer cup (44) is in fluid communication with cutter lumen (52) via a first port (45); and is in fluid communication with vacuum pump (38) via a second port (47). A conduit (39) couples port (41) of vacuum pump (38) with second port (47) of outer cup (44). A spring-loaded seal (not shown) or other feature may optionally be provided on conduit (39) and/or second port (47) and/or port (41) of vacuum pump (38), to substantially seal tissue sample holder (40) and/or vacuum pump (38) when conduit (39) is disconnected from tissue sample holder (40) or vacuum pump (38) and/or when probe (12) is decoupled from holster (14). In the present example, second port (47) is further coupled with a hydrophobic filter (48), which is in fluid communication with the interior space defined by outer cup (44). Hydrophobic filter (48) is configured to permit vacuum pump (38) to induce a vacuum in tissue sample holder (40) while preventing liquids from being communicated from tissue sample holder (40) to vacuum pump (38). In addition to or in lieu of having hydrophobic filter (48) a highly absorbent material may be provided in tissue sample holder (40) to soak up liquids. Alternatively, liquids may be dealt with in any other suitable fashion. As described in greater detail below, the vacuum created in tissue sample holder (40) by vacuum pump (38) is communicated to cutter (50) in the present example. In particular, vacuum pump (38) may thus be used to induce a vacuum in cutter lumen (52); with such a vacuum being communicated through conduit (39), ports (41, 45, 47), and the interior of outer cup (44).

Filter tray (46) of the present example has a basket-like configuration, and has plurality of openings (47) formed therethrough. Openings (47) are sized and configured to permit the passage of fluids therethrough while preventing the passage of tissue samples therethrough. Filter tray (46) is thus configured to receive tissue samples that are communicated proximally through cutter (50) as will be described in greater detail below. It should be understood that filter tray (46) may take a variety of alternate forms. By way of example only, a plurality of slits or other features may be formed through filter tray (46) in addition to or in lieu of round openings (47). As another merely illustrative alternative, filter tray (46) may be substituted with a textile mesh and/or other structure(s) or component(s).

Cap (42) is removably coupled with outer cup (44) in the present example. A pair of latches (56) provide selective engagement between cap (42) and outer cup (44). In particular, latches (56) engage a lip (57) of outer cup (44). Lip (57) has gaps (59) permitting passage of latches (56), such that a user may secure cap (42) to outer cup (44) by aligning latches (56) with gaps (59), pushing cap (42) onto outer cup (44), then rotating cap (42) past gaps (59) to engage latches (56) with lip (57). Alternatively, cap (42) may be secured to outer cup (44) in any other suitable fashion. An o-ring (53) provides a seal when cap (42) is engaged with outer cup (44). A vacuum may thus be maintained within outer cup (44) when cap (42) is secured to outer cup (44). In operation, a user may remove cap (42) to access tissue samples that have gathered on filter tray (46) during a biopsy process. In the present example, cap (42) is removed by rotating cap (42) to align latches (56) with gaps (59), then pulling cap (42) off. Of course, cap (42) may be removed from outer cup (44) in any other suitable fashion.

Tissue sample holder (40) of the present example is configured to hold at least ten tissue samples. Alternatively, tissue sample holder (40) may be configured to hold any other suitable number of tissue samples. It should be understood that, as with other components described herein, tissue sample holder (40) may be varied, modified, substituted, or supplemented in a variety of ways; and that tissue sample holder (40) may have a variety of alternative features, components, configurations, and functionalities.

For instance, tissue sample holder (40) may be alternatively configured such that it has a plurality of discrete tissue sample compartments that may be selectively indexed to cutter lumen (52). Such indexing may be provided automatically or manually. By way of example only, tissue sample holder (40) may be configured and operable in accordance with the teachings of U.S. Pub. No. 2008/0195066, entitled "Revolving Tissue Sample Holder for Biopsy Device," published Aug. 14, 2008, the disclosure of which is incorporated by reference herein; U.S. Pat. Pub. No. 2010/0160826, entitled "Tissue Biopsy Device with Rotatably Linked Thumbwheel and Tissue Sample Holder," published Jun. 24, 2010; U.S. Pat. Pub. No. 2010/0160824, entitled "Biopsy Device with Discrete Tissue Chambers," published Jun. 24, 2010, the disclosure of which is incorporated by reference herein; or U.S. Pat. Pub. No. 2010/0160816 12/337,87'1, entitled "Mechanical Tissue Sample Holder Indexing Device," published June 24, 2010, the disclosure of which is incorporated by reference herein. Other suitable alternative versions, features, components, configurations, and functionalities of tissue sample holder (40) will be apparent to those of ordinary skill in the art in view of the teachings herein. Alternatively, tissue sample holder (40) may simply be omitted, if desired.

Exemplary Cutter

Figure 5:
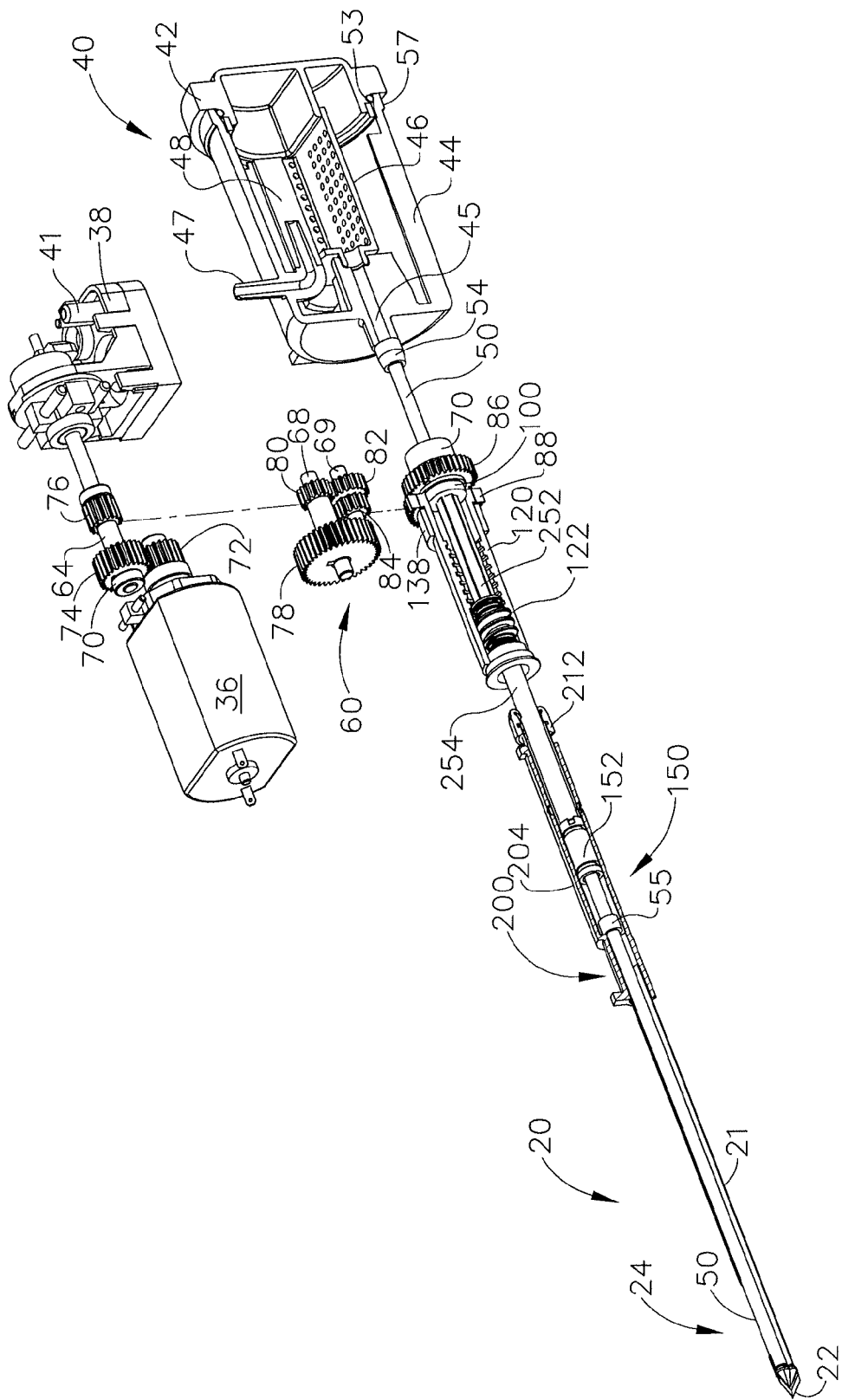
FIG. 5 depicts an exploded view of the biopsy device components of FIG. 4, with portions shown in cross-section, and with a battery and a circuit board removed.

As shown in FIGS. 8-9 (among others), cutter (50) of the present example is substantially hollow, such that cutter (50) defines a cutter lumen (52). Cutter (50) also has a substantially sharp distal edge (51), such that cutter (50) is operable to sever a biopsy sample from tissue protruding through lateral aperture (24) of needle (20). Alternatively, the distal end of cutter (50) may have any other suitable configuration. As shown in FIGS. 3 and 5-6, a proximal portion of cutter (50) extends into tissue sample holder (40). A vacuum created in tissue sample holder (40) by vacuum pump (38) is thus communicated to cutter lumen (52). A seal (54) is provided at the interface of cutter (50) and outer cup (44). Seal (54) is configured to substantially seal the interface of cutter (50) and mount (42), even as cutter (50) rotates and translates relative to outer cup (44). Furthermore, cutter (50) is configured such that it remains in sealed fluid communication with the interior of tissue sample holder (40) even when cutter (50) is in a distal most position. For instance, the length of cutter (50) may be such that at least a portion of cutter (50) is always disposed in outer cup (44) of tissue sample holder (40) during operation of biopsy device (10). Of course, cutter (50) may have any other suitable alternative features or configurations. Similarly, cutter (50) may have any other suitable alternative relationships with tissue sample holder (40).

It should be understood that, as with other components described herein, cutter (50) may be varied, modified, substituted, or supplemented in a variety of ways; and that cutter (50) may have a variety of alternative features, components, configurations, and functionalities. Suitable alternative versions, features, components, configurations, and functionalities of cutter (50) will be apparent to those of ordinary skill in the art in view of the teachings herein.

Exemplary Cutter Actuation Mechanism

As shown in FIGS. 3-7 and 10-11 (among others), cutter actuation mechanism (60) of the present example comprises motor (36), shafts (62, 64), and gears (72, 74, 76), each of which are described in greater detail above. Cutter actuation mechanism (60) further comprises a fourth gear (78), which meshes with third gear (76). Fourth gear (78) is unitarily secured to a third shaft (68), which is supported in body (30) by bearings (70). A fifth gear (80) is also unitarily secured to third shaft (68). Gears (78, 80) thus rotate unitarily with third shaft (68) in this example. Fifth gear (80) meshes with sixth gear (82), which is unitarily secured to a fourth shaft (69). Fourth shaft (69) is also supported in body (30) by bearings (70). A seventh gear (84) is also unitarily secured to fourth shaft (69). Gears (82, 84) thus rotate unitarily with fourth shaft (69) in this example. It should be understood in view of the foregoing that activation of motor (36) will rotate gears (82, 84) in the present example.

As shown in FIGS. 3 and 6, motor (36), shafts (62, 64, 68, 69), gears (72, 74, 76, 78, 80, 82, 84), and bearings (70) are all contained within holster (14) in the present example. As shown in FIG. 2, gears (82, 84) are partially exposed by an opening formed in a cover plate (18) of holster (14) in the present example.

Cutter actuation mechanism (60) of the present example further comprises a hex nut (100) and a worm nut (120). Hex nut (100) includes a gear (86), which is configured to rotate unitarily with hex nut (100). Worm nut (120) also includes a gear (88), which is configured to rotate unitarily with worm nut (120). Gear (86) is configured to mesh with gear (82) when probe (12) and holster (14) are coupled together; while gear (88) is configured to mesh with gear (84) when probe (12) and holster (14) are coupled together. In particular, and as shown in FIG. 2, gears (86, 88) are partially exposed by an opening formed in a cover plate (16) of probe (12) in the present example. Motor (36) is thus operable to rotatingly drive gears (86, 88) in the present example when probe (12) and holster (14) are coupled together. As described in greater detail below, such rotation of gears (86, 88) will cause cutter (50) to rotate and translate in the present example.

A sleeve (250) is unitarily secured to cutter (50). As best seen in FIG. 8, sleeve (250) comprises a hex portion (252), a smooth portion (254), and a flange (256) separating hex portion (252) from smooth portion (254). In the present example, sleeve (250) is overmolded about cutter (50), such that cutter (50) and sleeve (250) rotate and translate unitarily. For instance, sleeve (250) may be formed of a plastic material that is overmolded about a metal cutter (50). Alternatively, any other suitable materials and methods of forming may be used for sleeve (250) and cutter (50), and sleeve (250) may be secured to cutter (50) in any other suitable fashion (e.g., using set screw, bonding, etc.). Hex nut (100) is slidably positioned over hex portion (252) of sleeve (250). In particular, hex portion (252) of sleeve (250) presents six flat faces; while hex nut (100) defines a hexagonal opening with six flat faces that are configured to complement the flat faces of sleeve (250). The engagement between sleeve (250) and hex nut (100) is therefore such that rotation of hex nut (100) provides corresponding rotation of sleeve (250). The engagement between sleeve (250) and hex nut (100) is also such that hex nut (100) may slide longitudinally relative to sleeve (250), even as hex nut (100) and sleeve (250) simultaneously rotate. For instance, the longitudinal position of hex nut (100) may stay substantially constant as cutter (50) and sleeve (250) translate longitudinally. Bosses (not shown) are formed in the housing of probe (12) in the present example to maintain the longitudinal position of hex nut (100), while also permitting hex nut (100) to rotate. Hex nut (100) is further supported by a bearing (70) in the present example. It should also be understood that sleeve (250) and hex nut (100) may have a variety of other configurations (e.g., complementary key and keyway instead of hex features, etc.) and relationships. Similarly, a variety of other structures or components may be used in addition to or in lieu of sleeve (250) and/or hex nut (100).

As noted above, gear (86) of hex nut (100) is configured to mesh with gear (82), such that rotation of gear (82) causes rotation of hex nut (100). Such rotation of hex nut (100) will cause corresponding rotation of cutter (50) as noted above. It will therefore be understood that cutter actuation mechanism (60) may cause rotation of cutter (50) in response to activation of motor (36), with rotation of motor (36) being communicated to cutter (50) through shafts (62, 64, 68, 69), gears (72, 74, 76, 78, 80, 82, 84, 86), hex nut (100), and sleeve (250). Of course, any other suitable structures, components, configurations, or techniques may be used to provide rotation of cutter (50).

Cutter actuation mechanism (60) of the present example further comprises a lead screw (122). Lead screw (122) is positioned about hex portion (252) of sleeve (250), and is configured to rotate unitarily therewith. As noted above, hex portion (252) of sleeve (250) presents six flat faces. Lead screw (122) defines a hexagonal opening with six flat faces that are configured to complement the flat faces of sleeve (250). The engagement between sleeve (250) and lead screw (122) is therefore such that rotation of cutter (50) and sleeve (250) provides corresponding rotation of lead screw (122). Lead screw (122) is further secured to hex portion (252) of sleeve (250) by a clip (124). In particular, clip (124) is secured to sleeve (250), and a washer (126) is positioned between clip (124) and lead screw (122). Washer (126) and clip (124) are configured such that washer (126) may not move proximally past clip (124). A first coil spring (128) is positioned between the proximal end of lead screw (122) and washer (126). A second coil spring (130) is positioned between the distal end of lead screw (122) and flange (256) of sleeve (250). Flange (256), washer (126), and clip (124) thus restrict longitudinal motion of lead screw (122) along sleeve (250). The spacing between flange (256) and washer (126) permit some freedom of movement for lead screw (122) along a portion of the length of sleeve (250) between flange (256) and washer (126); while springs (128, 130) bias lead screw (122) to be substantially centered between flange (256) and washer (126). It should be understood that any other suitable type of resilient member may be used in addition to or in lieu of coil springs (128, 130).

Lead screw (122) has external threads (132) that are engaged with internal threads (134) of worm nut (120). Accordingly, lead screw (122) translates relative to worm nut (120) when lead screw (122) rotates relative to worm nut (120) when threads (132, 134) are engaged. However, the interior length of worm nut (120) also includes smooth sections (136) that are distal to and proximal to internal threads (134). Thus, lead screw (122) may not translate relative to worm nut (120) when lead screw (122) rotates relative to worm nut (120) when threads (132) are located at smooth sections (136) (e.g., when threads (132, 134) are not engaged). Threads (132) of lead screw (122) are relatively coarse in the present example, which may allow repeated engagement and disengagement between threads (132, 134) without substantially damaging threads (132).

Bosses (not shown) are formed in the housing of probe (12) in the present example to maintain the longitudinal position of worm nut (120), while also permitting worm nut (120) to rotate. Worm nut (120) is further supported by a bushing (138) in the present example. It should be understood that, due to engagement of lead screw (122) with flange (256) and washer (126), and due to engagement of sleeve (250) with cutter (250), translation of lead screw (122) relative to worm nut (120) in the present example also results in translation of cutter (50) relative to body (30) in the present example. It should also be understood that sleeve (250), lead screw (122), and worm nut (1 20) may have a variety of other configurations and relationships. Similarly, a variety of other structures or components may be used in addition to or in lieu of sleeve (250) and/or worm nut (120).

As noted above, gears (82, 84) of holster (14) rotate simultaneously when motor (36) is activated. As further noted above, gears (82, 84) mesh with gears (86, 88) of probe (12) when probe (12) is coupled with holster (14), such that activated motor (36) rotates gears (86, 88) simultaneously. Activated motor (36) will thus rotate hex nut (100) and worm nut (120) simultaneously. It should therefore be understood that sleeve (250), cutter (50), lead screw (122), and worm nut (120) will all rotate simultaneously when motor (36) is activated. It is also noted that gears (82, 84) have different pitch diameters (i.e., the pitch diameter of gear (82) is different from the pitch diameter of gear (84)). Gears (86, 88) also have different pitch diameters (i.e., the pitch diameter of gear (86) is different from the pitch diameter of gear (88)). Accordingly, even with motor (36) rotating at one rotational speed, hex nut (100) and worm nut (120) rotate simultaneously in the same direction at different rotational speeds. Since rotation of lead screw (122) is driven by rotation of hex nut (100), lead screw (122) and worm nut (120) also rotate simultaneously in the same direction at different rotational speeds. Even though lead screw (122) and worm nut (120) rotate simultaneously in the same direction, the difference between rotational speeds of lead screw (122) and worm nut (120) provide a net result of lead screw (122) rotating relative to worm nut (120), such relative rotation provides translation of cutter (50) as cutter (50) rotates. By way of example only, with motor (36) providing an output speed of approximately 8,000 rpm, the above-described configuration may provide rotation of cutter (50) at a speed of approximately 1,000 rpm and rotation of worm nut (120) at a speed of approximately 850 rpm, resulting in a net rotation of cutter (50) relative to worm nut (120) at approximately 150 rpm. Of course, any other suitable differential may be provided.

In the present example, cutter (50) is retracted proximally when motor (36) is activated to rotate cutter (50) counterclockwise (viewed from tissue sample holder (40) toward needle (20)); while cutter (50) is advanced distally when motor (36) is activated to rotate cutter (50) clockwise (viewed from tissue sample holder (40) toward needle (20)). The direction of motor (36) rotation may thus be reversed to transition between distal and proximal translation of cutter (50). Alternatively, cutter actuation mechanism (60) may be configured to be self-reversing, such that cutter (50) may be translated distally and proximally without reversing the direction of motor (36) rotation.

Figure 14:
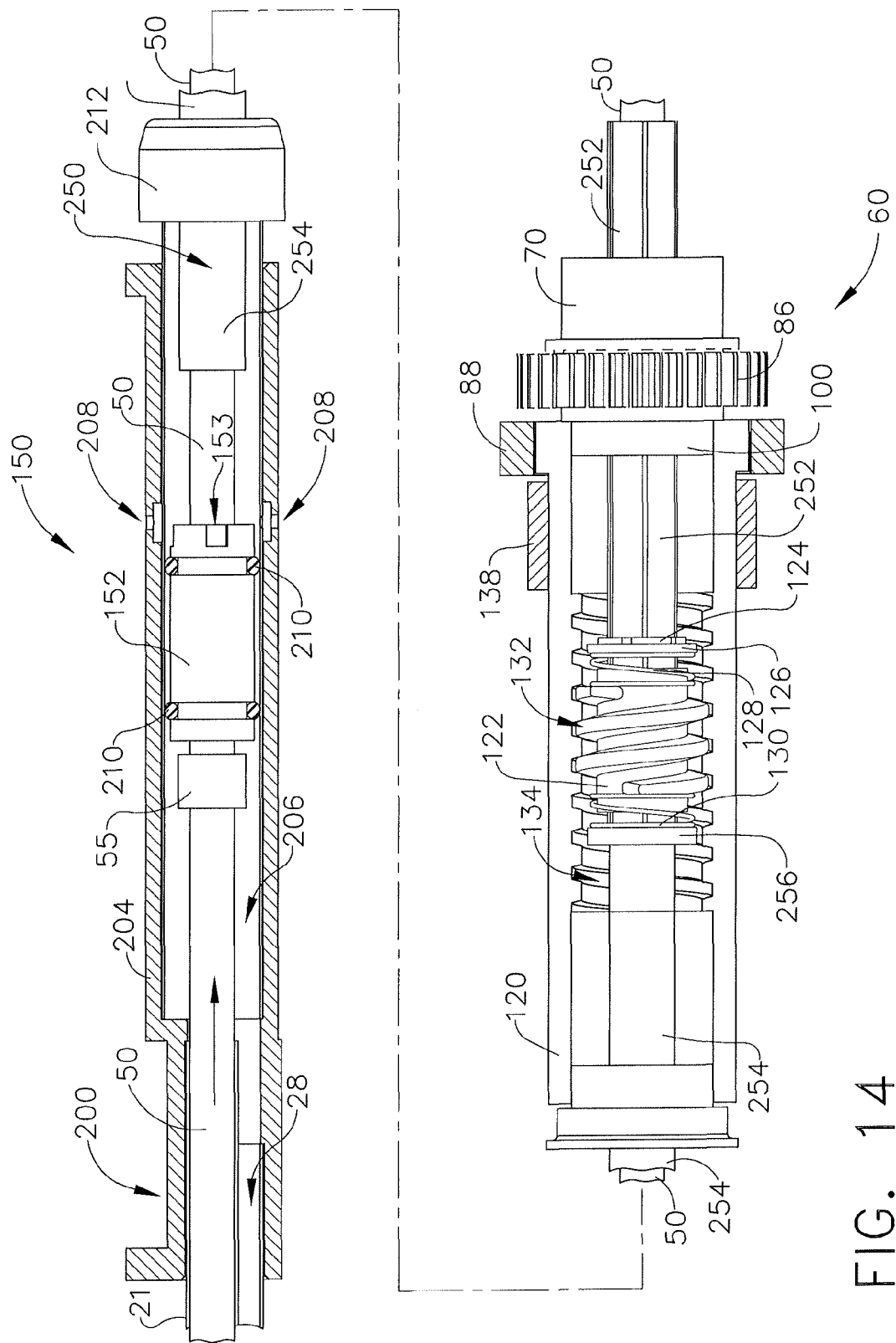
FIG. 14 depicts a side cross-sectional view of the components of FIG. 10, with the cutter in the partially retracted position of FIG. 12.

In one merely illustrative example of operation of cutter actuation mechanism (100), cutter (50) may be initially located in a distal-most position, such that lateral aperture (24) is "closed" as shown in FIG. 9; with lead screw (122) being positioned at the distal smooth section (136) of worm nut (120), as shown in FIGS. 10-11. Spring (130) biases lead screw (122) proximally to engage threads (132) with threads (134). At this stage, clockwise rotation of cutter (50) relative to worm nut (120) will not result in any translation of cutter (50) (e.g., lead screw (122) will essentially "freewheel"); while counterclockwise rotation of cutter (50) relative to worm nut (120) will result in proximal translation of cutter (50). As cutter (50) is rotated by motor (36) and cutter actuation mechanism (60) in the counterclockwise direction (viewed from tissue sample holder (40) toward needle (20)), cutter actuation mechanism (100) causes cutter (50) to retract proximally, as shown in FIGS. 12-14. As noted above, such proximal or rearward translation may be effected through engagement of threads (132, 134), and due to lead screw (122) rotating at a faster speed than worm nut (120). Lead screw (122) continues to traverse threads (134) of worm nut (120) as cutter (50) continues to retract proximally.

Figure 20:
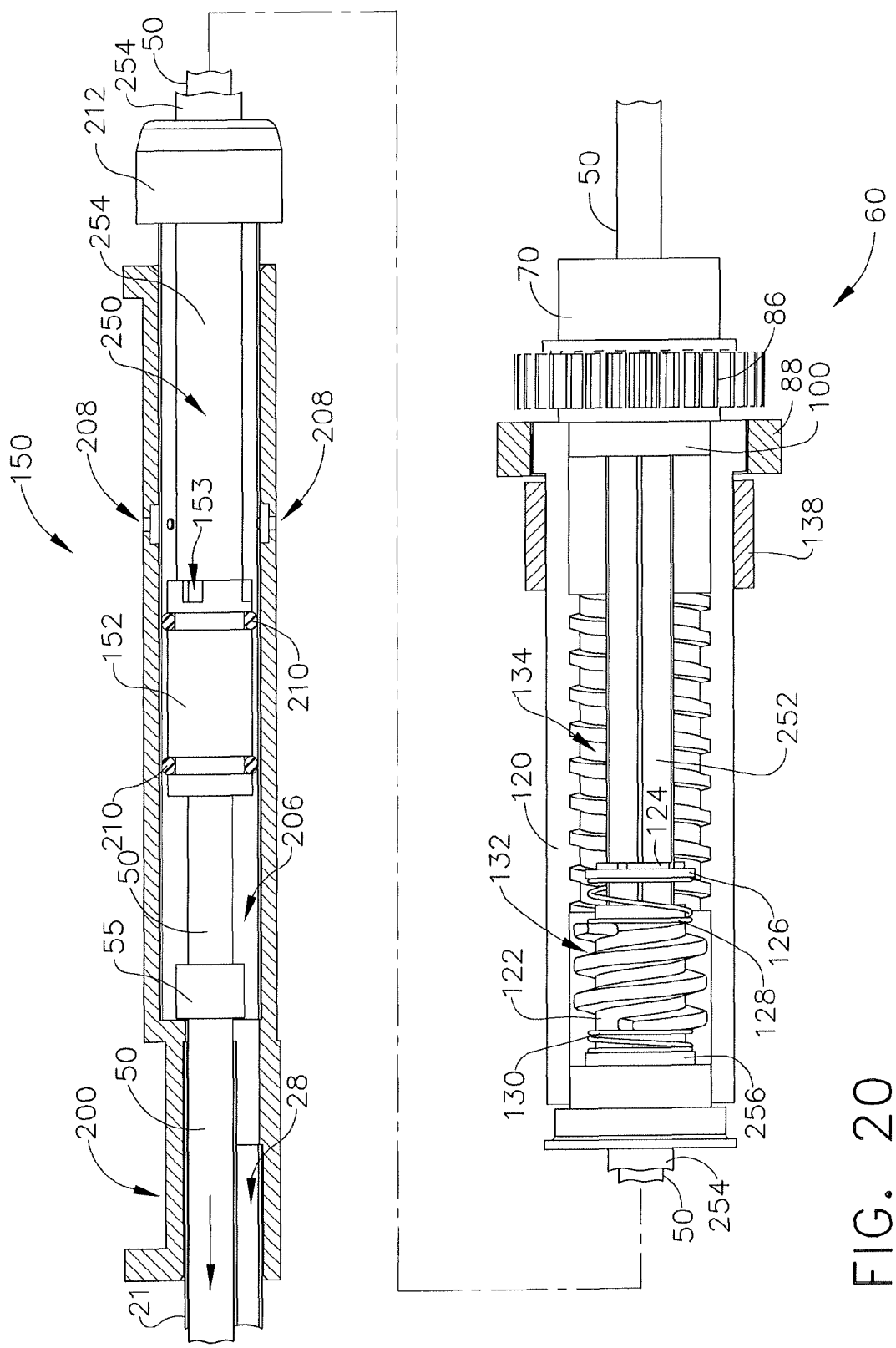
FIG. 20 depicts a side cross-sectional view of the components of FIG. 10, with the cutter re-advanced to the distal-most position of FIG. 9.

Cutter (50) then reaches a proximal-most position, such that lateral aperture (24) is "opened" as shown in FIG. 15. At this stage, lead screw (122) is positioned at the proximal smooth section (136) of worm nut (120), as shown in FIGS. 16-17. Spring (128) biases lead screw (122) distally to engage threads (132) with threads (134). At this stage, continued counterclockwise rotation of cutter (50) relative to worm nut (120) will not result in any translation of cutter (50) (e.g., lead screw (122) will essentially "freewheel"); while clockwise rotation of cutter (50) relative to worm nut (120) will result in distal translation of cutter (50). To that end, motor (36) may again be activated, with its rotation direction being reversed to reverse the rotation direction of cutter (50) and associated components. In particular, reversing the rotational direction of motor (36) causes cutter (50) to rotate clockwise (viewed from tissue sample holder (40) toward needle (20)). Such clockwise rotation of cutter (50) causes cutter to advance distally to reach the distal-most position again, as shown in FIGS. 18-20.

While cutter (50) is shown and described above as rotating counterclockwise (viewed from tissue sample holder (40) toward needle (20)) during retraction of cutter (50) and clockwise (viewed from tissue sample holder (40) toward needle (20)) during advancement of cutter (50), it should be immediately apparent to those of ordinary skill in the art that cutter (50) may instead be rotated clockwise during retraction of cutter (50) and counterclockwise during advancement of cutter. For instance, such reversal may be provided by reversing the orientation of threads (132, 134). Alternatively, such reversal may be provided by changing the differential such that worm nut (120) rotates faster than cutter (50). Of course, any other suitable structures, components, configurations, or techniques may be used to provide translation and/or rotation of cutter (50). It should therefore be understood that, as with other components described herein, cutter actuation mechanism (60) may be varied, modified, substituted, or supplemented in a variety of ways; and that cutter actuation mechanism (60) may have a variety of alternative features, components, configurations, and functionalities. By way of example only, biopsy device (10) may be configured such that cutter (50) does not translate (e.g., such that cutter (50) merely rotates, etc.); or such that cutter (50) does not rotate (e.g., such that cutter (50) merely translates, etc.). Other suitable alternative versions, features, components, configurations, and functionalities of cutter actuation mechanism (60) will be apparent to those of ordinary skill in the art in view of the teachings herein.

Exemplary Pneumatic Operation

As noted above, vacuum pump (38) is operable to induce a vacuum in tissue sample holder (40), and such vacuum may be further communicated to cutter lumen (52). In particular, vacuum pump (38) may start building a vacuum in cutter lumen (52) as soon as motor (36) is activated; and such a vacuum may continue to build or be maintained as cutter (50) starts moving proximally toward the retraced position. At this stage, second lumen (28) is vented to atmosphere. In particular, shuttle valve slider (152) is in a distal position, allowing atmospheric air to reach second lumen (28)—via openings (208), notches (152), the gap between the inner diameter of shuttle valve slider (152) and the outer diameter of cutter (50), and the portion of sleeve interior (206) that is distal to shuttle valve slider (152)—as shown in FIGS. 10-11. Alternatively, second lumen (28) may be fluidly coupled with vacuum pump (38), such that a vacuum is created in second lumen (28) at this stage.

As cutter (50) moves toward retracted position, such that lateral aperture (24) of needle (20) is "partially open" as shown in FIG. 12, a vacuum in cutter lumen (52) may be further communicated through first lumen (26), which may draw tissue into lateral aperture (24). At this stage, second lumen (28) is still vented to atmosphere. In particular, due to the "lost motion" between cutter (50) and shuttle valve slider (152), shuttle valve slider (152) remains in the distal position despite proximal retraction of cutter (50), as shown in FIGS. 13-14. Alternatively, second lumen (28) may be fluidly coupled with vacuum pump (38), such that a vacuum is created in second lumen (28) at this stage. In the present example, second lumen (28) is substantially sealed when cutter (50) reaches a longitudinal position that is proximal to the position shown in FIG. 12, and before cutter (50) reaches the fully retracted position shown in FIG. 15.

When cutter (50) reaches the fully retracted position, such that lateral aperture (24) of needle (20) is "open" as shown in FIG. 15, a vacuum in cutter lumen (52) may continue to be further communicated through first lumen (26), which may continue to draw tissue into lateral aperture (24). Of course, some amount of tissue may naturally prolapse into lateral aperture (24) without the assistance of vacuum, such that vacuum may not even be needed to draw tissue into lateral aperture (24). At this stage, second lumen (28) is substantially sealed relative to atmosphere, as shown in FIGS. 16-17. In particular, stop member (55) has pushed shuttle valve slider (152) to a proximal position, such that o-rings (210) "straddle" openings (208) and seal against the interior sidewall of sleeve portion (204) to prevent atmospheric air from being communicated from openings (208) to second lumen (28) via hollow interior (206) of sleeve portion (204).

As motor (36) is reversed and cutter (50) is advanced to sever tissue protruding through lateral aperture (24), as shown in FIGS. 18-20, vacuum pump (38) may continue to induce a vacuum in cutter lumen (52), and second lumen (28) may eventually be vented to atmosphere. However, in the initial stages of advancement of cutter (50) from the proximal-most position to the distal-most position, the "lost motion" between cutter (50) and shuttle valve slider (152) leaves shuttle valve slider (152) in the proximal position until cutter (50) advances far enough for the distal end of sleeve (250) to engage the proximal end of shuttle valve slider (152). Until such engagement between the distal end of sleeve (250) and the proximal end of shuttle valve slider (152), o-rings (210) of shuttle valve slider (152) continue to substantially seal second lumen (28) from openings (208). After the distal end of sleeve (250) engages the proximal end of shuttle valve slider (152), and after cutter (50) has continued to move distally to a sufficient degree, the distal end of sleeve (250) eventually pushes shuttle valve slider (152) distally, such that the proximal-most o-ring (210) is eventually moved distal to openings (208). With shuttle valve slider (152) reaching such a position (and positions that are further distal to such a position), second lumen (28) is again vented to atmosphere as described above, and as shown in FIGS. 19-20. As cutter (50) again finally reaches the distal-most position, as shown in FIG. 18, cutter (50) may completely sever the tissue protruding through lateral aperture (24), with second lumen (28) being vented as shown in FIGS. 19-20.

With the severed tissue sample residing in cutter lumen (52), with vacuum pump (38) drawing a vacuum at the proximal face of the severed tissue sample, and with the venting being provided at the distal face of the severed tissue sample (via openings (208), second lumen (28), and openings (27)), the pressure differential applied to the severed tissue sample may cause the severed tissue sample to be drawn proximally through cutter lumen (52) and into tissue sample holder (40). The severed tissue sample may thus be deposited on filter tray (46) of tissue sample holder (40).

Of course, any other suitable structures, components, configurations, or techniques may be used to provide selective sealing and/or venting of second lumen (28). By way of example only, while shuttle valve slider (152) is actuated mechanically based on the axial position of cutter (50) in the present example, it should be understood that shuttle valve slider (152) or any other type of valve may instead be actuated electrically (e.g., via a separate motor or solenoid), pneumatically, or otherwise. Furthermore, in some variations of biopsy device (10), a vacuum, saline, pressurized air, atmospheric air, and/or any other medium may be communicated to second lumen (28) at any suitable stage of operation of biopsy device (10) (e.g., applying vacuum or venting to second lumen (28) during and/or upon retraction of cutter (50) and/or during advancement of cutter (50), sealing second lumen during advancement of cutter (50), etc.). Suitable alternative structures, components, configurations, or techniques for communicating severed tissue samples proximally through cutter lumen (52) to reach tissue sample holder (40) will be apparent to those of ordinary skill in the art in view of the teachings herein.

Exemplary Method of Operation

In a merely exemplary use of biopsy device (10), a user first inserts tissue piercing tip (22) into the breast of a patient. During such insertion, cutter (50) may be advanced to the distal-most position, such that lateral aperture (24) of needle (20) is closed as shown in FIGS. 9-11. As also noted herein, such insertion may be performed under visual guidance, stereotactic guidance, ultrasound guidance, MRI guidance, PEM guidance, BSGI guidance, palpatory guidance, some other type of guidance, or otherwise. With needle (20) sufficiently inserted into the patient's breast, the user may then activate motor (36), which may in turn activate vacuum pump (38) and cutter actuation mechanism (100). Such activation of vacuum pump (38) may induce a vacuum in tissue sample holder (40) and cutter lumen (52) as described above. Such activation of cutter actuation mechanism (60) may cause cutter (50) to rotate counterclockwise and translate proximally, as shown in FIGS. 12-14. As cutter (50) starts retracting and when cutter (50) reaches the retracted position, vacuum from vacuum pump (38) (as communicated through tissue sample holder (40) and cutter lumen (52)) may draw tissue into lateral aperture (24) of needle (20). During this time, second lumen (28) may be vented by valve mechanism (150).

Once cutter (50) reaches a proximal-most position, as shown in FIGS. 15-17, vacuum may still be communicated through vacuum lumen (52) and first lumen (26), drawing tissue into lateral aperture (24) of needle (20). Second lumen (28) is substantially sealed by valve assembly (150) at this time, as shown in FIGS. 16-17. In addition, lead screw (122) freewheels yet is biased distally by spring (128) as cutter (50) continues to rotate counterclockwise. Lateral aperture (24) is fully open at this stage, with tissue prolapsed therein.

The rotation direction of motor (36) is then reversed and cutter (50) begins to advance distally until again reaching the distal-most position as shown in FIGS. 18-20. As cutter (50) advances distally, vacuum is still being communicated through vacuum lumen (52), helping to hold tissue in place as sharp distal edge (51) of cutter (50) begins to sever the tissue. Second lumen (28) is initially substantially sealed by valve assembly (150) at this time, but is eventually vented as shown in FIGS. 19-20. Cutter (50) then reaches the distal-most position, as shown in FIGS. 18-20, thereby "closing" lateral aperture (24), and such that sharp distal edge (51) of cutter (50) completely severs the tissue. Vacuum is still being communicated through cutter lumen (52) at this time, and valve assembly (150) vents second lumen (28) as shown in FIGS. 19-20. As described above, this combination of vacuum and venting provides communication of the severed tissue sample proximally through cutter lumen (52) and into tissue sample holder (40). Motor (36) may continue to operate at the end of the cutting stroke, thereby continuing to drive vacuum pump (38) to maintain a vacuum in tissue sample holder (40). In addition, spring (130) biases lead screw (122) proximally to engage threads (132), while allowing cutter (50) to continue rotating at the distal-most position. A cutting stroke will thus be complete, and may be initiated as many times as desired to acquire additional tissue samples.

As noted above, several cutting strokes may be performed to acquire several tissue samples without the user having to withdraw needle (20) from the patient's breast. The user may adjust the orientation of lateral aperture (24) about the axis defined by needle (20) by rotating the entire biopsy device (10) between cutting strokes for multiple sample acquisition. Alternatively, biopsy device (10) may be configured such that needle (20) is rotatable relative to body (30), such that needle (20) may be rotated via a thumbwheel or other feature. Once the desired number of tissue samples have been obtained, the user may withdraw needle (20) from the patient's breast. The user may then remove cap (42) from cup (44) and retrieve the tissue samples from filter tray (46).

At the end of a procedure, the user may separate probe (12) from holster (14). Holster (14) may then be cleaned and/or sterilized for subsequent use. Probe (12) may be disposed of. Alternatively, as noted above, biopsy device (10) may alternatively be formed as a unitary construction, such that there is no probe (12) separable from a holster (14).

It should be understood that any of a variety of operations may occur at the end of a cutting stroke. For instance, biopsy device (10) may provide a variety of forms of feedback to inform the user that a cutting stroke as been completed. By way of example only, biopsy device (10) may provide an electronic beep or other audible indication, a mechanical audible indication (e.g., a loud click), a visual indication (e.g., a light illuminating or flashing), or some other type of audible and/or visual indication. Alternatively, and particularly in versions where cup (44) is transparent, the user may know that a cutting stroke is complete by simply watching tissue sample holder (40) until the user sees a tissue sample being deposited on filter tray (46). Alternatively, a control module may be provided to automatically deactivate motor (36) as soon as a cutting stroke is complete, even if the user continues to hold a trigger button (not shown) down. The user may then initiate another cutting stroke by releasing and then re-pressing the trigger button. As yet another merely illustrative example, and as noted above, a control module may initiate a cutting stroke in response to the user briefly pressing or tapping a trigger button, and may automatically deactivate motor (36) as soon as the cutting stroke is complete. The user may then initiate another cutting stroke by briefly pressing or tapping the trigger button again. Still other suitable ways in which biopsy device (10) may operate at the end of a cutting stroke and/or to initiate a subsequent cutting stroke will be apparent to those of ordinary skill in the art in view of the teachings herein.

It should also be understood that circuit boards (35) may include circuitry that is configured to automatically cause the rotational direction of motor (36) to reverse as soon as cutter (50) reaches the proximal-most position. For instance, one or more sensors (e.g., hall effect sensor, etc.) may track or otherwise sense the longitudinal position of cutter (50). In addition or in the alternative, one or more sensors (e.g., encoder with encoder wheel, etc.) may track or otherwise sense the number of rotations of cutter (50), and control circuitry may understand the longitudinal position of cutter (50) as a function of the number of rotations of cutter (50). As yet another alternative, motor reversal may be essentially manual (e.g., such that biopsy device (10) includes a "forward" button and a "reverse" button, etc.). Still other suitable ways in which the rotational direction of motor (38) may be manually or automatically reversed will be apparent to those of ordinary skill in the art in view of the teachings herein. It should also be understood that one or both circuit boards (35) may continue to operate motor (36) at least temporarily (e.g., for a few seconds, etc.) at the end of each cutter (50) stroke (e.g., while cutter (50) remains at the distal-most position and/or at the proximal-most position), such as to continue to operate vacuum pump (38).

In versions of biopsy device (10) where an electronic based audible and/or visual indication of the end of a cutting stroke is provided, as well as versions of biopsy device (10) where a control module automatically deactivates motor (36) or disengages a clutch or provides some other type of automated response, there are a variety of ways in which the end of a cutting stroke may be sensed. For instance, a portion of cutter (50) may include a magnet, and a hall effect sensor may be positioned in body (30) to sense the presence of the magnet when cutter (50) reaches the distal-most position at the end of a cutting stroke. As another merely illustrative example, an encoder wheel may be coupled with cutter (50) or a rotating component of cutter rotation mechanism (60), such that the longitudinal position of cutter (50) may be determined based on a number of rotations. Other suitable ways in which the end of a cutting stroke may be sensed (e.g., electronically, mechanically, electro-mechanically, manually, etc.) will be apparent to those of ordinary skill in the art in view of the teachings herein.

Of course, the above examples of use of biopsy device (10) are merely illustrative. Other suitable ways in which biopsy device (10) may be used will be apparent to those of ordinary skill in the art in view of the teachings herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A method of biopsy device operation, wherein the biopsy device comprises a needle, a cutter, and a cutter actuation mechanism, wherein the cutter defines an internal lumen, wherein the cutter actuation mechanism comprises a first rotating member and a second rotating member, wherein the first rotating member is configured to rotate unitarily with the cutter, wherein the second rotating member is configured to rotate about the cutter, the method comprising:
- (a) drawing a vacuum in the internal lumen of the cutter;
- (b) rotating the first rotating member at a first rotational speed to rotate the cutter; and
- (c) rotating the second rotating member about the cutter at a second rotational speed to translate the cutter;

wherein the act of rotating the first rotating member and the act of rotating the second rotating member are performed simultaneously.

2. The method of claim 1, wherein the biopsy device further comprises a single motor in communication with the cutter actuation mechanism, the method further comprising initiating rotation of the single motor, wherein the single motor is operable to rotate the first rotating member and the second rotating member such that the act of rotating the first rotating member and the act of rotating the second rotating member are performed in response to the act of initiating rotation of the single motor.

3. The method of claim 2, wherein the biopsy device further comprises an integral vacuum pump in communication with the single motor, wherein the integral vacuum pump is operable to perform the act of drawing a vacuum in the internal lumen of the cutter, wherein the single motor is operable to drive the integral vacuum pump such that the act of drawing a vacuum in the internal lumen of the cutter is performed in response to the act of initiating rotation of the single motor.

4. The method of claim 1, wherein the first rotating member and the second rotating member are aligned along a common axis.

5. The method of claim 1, wherein the act of rotating the first rotating member further comprises rotating the first rotating member in a first rotational direction, wherein the act of rotating the second rotating member further comprises rotating the second rotating member in the first rotational direction.

6. The method of claim 5, wherein the act of rotating the first rotating member in the first rotational direction and the act of rotating the second rotating member in the first rotational direction are performed simultaneously.

7. The method of claim 1, further comprising reversing the direction of rotation of the first rotating member, such that the act of rotating the first rotating member further comprises:
- (i) rotating the first rotating member in a first rotational direction to rotate the cutter in the first rotational direction, and
- (ii) rotating the first rotating member in a second rotational direction to rotate the cutter in the second rotational direction;

wherein the act of rotating the first rotating member and the act of rotating the second rotating member are performed simultaneously before the act of reversing the direction of rotation of the first rotating member.

8. The method of claim 7, further comprising reversing the direction of rotation of the second rotating member, such that the act of rotating the second member further comprises:
- (i) rotating the second rotating member in a first rotational direction to translate the cutter in a first longitudinal direction, and
- (ii) rotating the second rotating member in a second rotational direction to translate the cutter in a second longitudinal direction;

wherein the act of rotating the first rotating member and the act of rotating the second rotating member are performed simultaneously before and after the act of reversing the direction of rotation of the second rotating member.

9. The method of claim 8, wherein the act of reversing the direction of rotation of the first rotating member and the act of reversing the direction of rotation of the second rotating member are performed simultaneously.

10. The method of claim 9, wherein the biopsy device further comprises a single motor in communication with the cutter actuation mechanism, the method further comprising:
- (a) rotating the motor in a first direction; and
- (b) reversing the direction of rotation of the motor to rotate the motor in a second direction.

11. The method of claim 10, wherein the act of reversing the direction of rotation of the first rotating member and the act of reversing the direction of rotation of the second rotating member are performed in response to the act of reversing the direction of rotation of the motor.

12. The method of claim 1, wherein the first rotating member comprises a threaded member unitarily secured to the cutter, wherein the act of rotating the first rotating member comprises rotating the threaded member to rotate unitarily with the cutter at the first rotational speed.

13. The method of claim 12, wherein the second rotating member comprises a nut positioned external to and coaxial with the threaded member, wherein the act of rotating the second rotating member comprises rotating the nut about the threaded member.

14. The method of claim 13, wherein the threaded member is rotated in a first rotational direction, wherein the nut is rotated in the first rotational direction while the threaded member is rotated in the first rotational direction, such that the difference between the first rotational speed and the second rotational speed provides relative rotation between the nut and the threaded member to cause the cutter to translate.

15. A method of biopsy device operation, wherein the biopsy device comprises a body, a needle, a cutter, and a shuttle valve slider, wherein the needle defines a first lumen and a second lumen and has an opening configured to fluidly couple the first lumen with the second lumen, the method comprising:
- (a) retracting the cutter in the first lumen from a first longitudinal position to a second longitudinal position, wherein the second longitudinal position is proximal to the first longitudinal position;
- (b) venting the second lumen to atmospheric air, wherein the act of venting the second lumen is performed during the act of retracting the cutter in the first lumen from the first longitudinal position to the second longitudinal position;
- (c) retracting the cutter in the first lumen from the second longitudinal position to a third longitudinal position, wherein the third longitudinal position is proximal to the second longitudinal position; and
- (d) sealing the second lumen relative to atmospheric air, wherein the act of sealing the second lumen relative to atmospheric air is performed during at least part of the act of retracting the cutter in the first lumen from the second longitudinal position to the third longitudinal position, wherein the act of sealing the second lumen relative to atmospheric air comprises moving the shuttle valve slider proximally.

16. The method of claim 15, wherein the shuttle valve slider is disposed coaxially about the cutter, wherein the act of moving the shuttle valve slider longitudinally is performed in response to the act of retracting the cutter in the first lumen from the second longitudinal position to the third longitudinal position.

17. The method of claim 16, wherein the cutter comprises a stop member configured to push the shuttle valve slider longitudinally, wherein the stop member is spaced apart from the shuttle valve slider during the act of retracting the cutter in the first lumen from the first longitudinal position to the second longitudinal position, wherein the stop member is engaged with the shuttle valve slider during the act of retracting the cutter in the first lumen from the second longitudinal position to the third longitudinal position.

18. The method of claim 15, further comprising advancing the cutter in the first lumen from the third longitudinal position to a fourth longitudinal position, wherein the fourth longitudinal position is distal to the third longitudinal position, wherein the shuttle valve slider is configured to seal the second lumen relative to atmospheric air during the act of advancing the cutter in the first lumen from the third longitudinal position to the fourth longitudinal position.

19. The method of claim 18, further comprising:
(a) advancing the cutter in the first lumen from the fourth longitudinal position to the first longitudinal position, wherein the first longitudinal position is distal to the fourth longitudinal position; and
(b) moving the shuttle valve slider distally to vent the second lumen to atmospheric air, wherein the act of moving the shuttle valve slider distally is performed during at least part of the act of advancing the cutter in the first lumen from the fourth longitudinal position to the first longitudinal position.

20. A method of biopsy device operation, wherein the biopsy device comprises a body, a needle, a cutter, and a shuttle valve slider, wherein the needle defines a first lumen and a second lumen and has an opening configured to fluidly couple the first lumen with the second lumen, the method comprising:
(a) retracting the cutter proximally within the first lumen through a first range of motion, wherein the cutter moves relative to the shuttle valve slider during the act of retracting the cutter proximally within the first lumen through the first range of motion, wherein the second lumen is vented to atmospheric air during the act of retracting the cutter proximally within the first lumen through the first range of motion;
(b) retracting the cutter proximally within the first lumen through a second range of motion; and
(c) moving the shuttle valve slider proximally to seal the second lumen relative to atmospheric air, wherein the act of moving the shuttle valve slider proximally is performed during the act of retracting the cutter proximally within the first lumen through the second range of motion, wherein the cutter and shuttle valve slider move together unitarily during the acts of retracting the cutter proximally within the first lumen through the second range of motion and moving the shuttle valve slider proximally.

* * * * *